US010306924B2

(12) United States Patent
DePiano et al.

(10) Patent No.: US 10,306,924 B2
(45) **Date of Patent: *Jun. 4, 2019**

(54) ATOMIZER FOR AN AEROSOL DELIVERY DEVICE FORMED FROM A CONTINUOUSLY EXTENDING WIRE AND RELATED INPUT, CARTRIDGE, AND METHOD

(71) Applicant: R. J. Reynolds Tobacco Company, Winston-Salem, NC (US)

(72) Inventors: John DePiano, Burlington, MA (US); David Smith, Needham, MA (US); Patsy Coppola, Bedford, MA (US); Charles Jacob Novak, III, Winston-Salem, NC (US); Steven Lee Alderman, Lewisville, NC (US); James William McClellan, Hollis, NH (US); John William Wolber, Nashua, NH (US); Frank S. Silveira, Wilmington, MA (US); Michael Laine, Newburyport, MA (US); Paul A. Brinkley, Winston-Salem, NC (US); Grady Lance Dooly, Winston-Salem, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 294 days.

This patent is subject to a terminal disclaimer.

(21) Appl. No.: 15/009,580

(22) Filed: Jan. 28, 2016

(65) Prior Publication Data

US 2016/0143364 A1 May 26, 2016

Related U.S. Application Data

(63) Continuation of application No. 13/827,994, filed on Mar. 14, 2013, now Pat. No. 9,277,770.

(51) Int. Cl.
*A61H 33/12* (2006.01)
*A61M 15/06* (2006.01)
(Continued)

(52) U.S. Cl.
CPC ............ *A24F 47/008* (2013.01); *H05B 3/03* (2013.01); *Y10T 29/49083* (2015.01)

(58) Field of Classification Search
None
See application file for complete search history.

(56) References Cited

U.S. PATENT DOCUMENTS 1,771,366 A 7/1930 Wyss et al.
2,057,353 A 10/1936 Whittemore, Jr.
(Continued)

FOREIGN PATENT DOCUMENTS

AU 276250 7/1965
CA 2 641 869 5/2010
(Continued)

OTHER PUBLICATIONS

U.S. Appl. No. 29/432,110, filed Sep. 13, 2012, Potter.
(Continued)

*Primary Examiner* — Thor S Campbell
(74) *Attorney, Agent, or Firm* — Womble Bond Dickinson (US) LLP

(57) ABSTRACT

The present disclosure relates to atomizers for an aerosol delivery device such as a smoking article. The atomizer may include a liquid transport element and a wire continuously extending along a longitudinal length thereof. The wire may define end portions, contact portions, and a heating portion. The wire may be continuously wound about the liquid transport element such that each of the portions of the wire defines coils. A related input, cartridge, and method of forming atomizers also provided.

24 Claims, 20 Drawing Sheets

(51) Int. Cl.
*A24F 47/00* (2006.01)
*H05B 3/03* (2006.01)

(56) References Cited

U.S. PATENT DOCUMENTS

| | | | |
|---|---|---|---|
| 2,104,266 | A | 1/1938 | McCormick |
| 2,805,669 | A | 9/1957 | Meriro |
| 3,200,819 | A | 8/1965 | Gilbert |
| 3,316,919 | A | 5/1967 | Green et al. |
| 3,378,673 | A | 4/1968 | Hopper |
| 3,398,754 | A | 8/1968 | Tughan |
| 3,419,015 | A | 12/1968 | Wochnowski |
| 3,424,171 | A | 1/1969 | Rooker |
| 3,476,118 | A | 11/1969 | Luttich |
| 3,678,249 | A | 7/1972 | Lennox |
| 4,054,145 | A | 10/1977 | Berndt et al. |
| 4,131,117 | A | 12/1978 | Kite et al. |
| 4,150,677 | A | 4/1979 | Osborne |
| 4,190,046 | A | 2/1980 | Virag |
| 4,219,032 | A | 8/1980 | Tabatznik et al. |
| 4,259,970 | A | 4/1981 | Green, Jr. |
| 4,284,089 | A | 8/1981 | Ray |
| 4,303,083 | A | 12/1981 | Burruss, Jr. |
| 4,449,541 | A | 5/1984 | Mays et al. |
| 4,506,682 | A | 3/1985 | Muller |
| 4,635,651 | A | 1/1987 | Jacobs |
| 4,667,084 | A | 5/1987 | Regge |
| 4,674,519 | A | 6/1987 | Keritsis et al. |
| 4,708,151 | A | 11/1987 | Shelar |
| 4,714,082 | A | 12/1987 | Banerjee et al. |
| 4,735,217 | A | 4/1988 | Gerth et al. |
| 4,756,318 | A | 7/1988 | Clearman et al. |
| 4,771,795 | A | 9/1988 | White et al. |
| 4,776,353 | A | 10/1988 | Lilja et al. |
| 4,793,365 | A | 12/1988 | Sensabaugh, Jr. et al. |
| 4,800,903 | A | 1/1989 | Ray et al. |
| 4,819,665 | A | 4/1989 | Roberts et al. |
| 4,821,749 | A | 4/1989 | Toft et al. |
| 4,830,028 | A | 5/1989 | Lawson et al. |
| 4,836,224 | A | 6/1989 | Lawson et al. |
| 4,836,225 | A | 6/1989 | Sudoh |
| 4,846,199 | A | 7/1989 | Rose |
| 4,848,374 | A | 7/1989 | Chard et al. |
| 4,848,376 | A | 7/1989 | Lilja et al. |
| 4,874,000 | A | 10/1989 | Tamol et al. |
| 4,880,018 | A | 11/1989 | Graves, Jr. et al. |
| 4,887,619 | A | 12/1989 | Burcham, Jr. et al. |
| 4,907,606 | A | 3/1990 | Lilja et al. |
| 4,913,168 | A | 4/1990 | Potter et al. |
| 4,917,119 | A | 4/1990 | Potter et al. |
| 4,917,128 | A | 4/1990 | Clearman et al. |
| 4,922,901 | A | 5/1990 | Brooks et al. |
| 4,924,888 | A | 5/1990 | Perfetti et al. |
| 4,928,714 | A | 5/1990 | Shannon |
| 4,938,236 | A | 7/1990 | Banerjee et al. |
| 4,941,483 | A | 7/1990 | Ridings et al. |
| 4,941,484 | A | 7/1990 | Clapp et al. |
| 4,945,931 | A | 8/1990 | Gori |
| 4,947,874 | A | 8/1990 | Brooks et al. |
| 4,947,875 | A | 8/1990 | Brooks et al. |
| 4,972,854 | A | 11/1990 | Kiernan et al. |
| 4,972,855 | A | 11/1990 | Kuriyama et al. |
| 4,986,286 | A | 1/1991 | Roberts et al. |
| 4,987,906 | A | 1/1991 | Young et al. |
| 5,005,593 | A | 4/1991 | Fagg |
| 5,019,122 | A | 5/1991 | Clearman et al. |
| 5,022,416 | A | 6/1991 | Watson |
| 5,038,458 | A | 8/1991 | Wagoner |
| 5,042,510 | A | 8/1991 | Curtiss et al. |
| 5,056,537 | A | 10/1991 | Brown et al. |
| 5,060,669 | A | 10/1991 | White et al. |
| 5,060,671 | A | 10/1991 | Count et al. |
| 5,065,775 | A | 11/1991 | Fagg |
| 5,072,744 | A | 12/1991 | Luke et al. |
| 5,074,319 | A | 12/1991 | White et al. |
| 5,076,296 | A | 12/1991 | Nystrom et al. |
| 5,093,894 | A | 3/1992 | Deevi et al. |
| 5,095,921 | A | 3/1992 | Losee et al. |
| 5,097,850 | A | 3/1992 | Braunshteyn et al. |
| 5,099,862 | A | 3/1992 | White et al. |
| 5,099,864 | A | 3/1992 | Young et al. |
| 5,103,842 | A | 4/1992 | Strang et al. |
| 5,121,757 | A | 6/1992 | White et al. |
| 5,129,409 | A | 7/1992 | White et al. |
| 5,131,415 | A | 7/1992 | Munoz et al. |
| 5,144,962 | A | 8/1992 | Counts et al. |
| 5,143,097 | A | 9/1992 | Sohn et al. |
| 5,146,934 | A | 9/1992 | Deevi et al. |
| 5,159,940 | A | 11/1992 | Hayward et al. |
| 5,159,942 | A | 11/1992 | Brinkley et al. |
| 5,179,966 | A | 1/1993 | Losee et al. |
| 5,211,684 | A | 5/1993 | Shannon et al. |
| 5,220,930 | A | 6/1993 | Gentry |
| 5,224,498 | A | 7/1993 | Deevi et al. |
| 5,228,460 | A | 7/1993 | Sprinkel et al. |
| 5,230,354 | A | 7/1993 | Smith et al. |
| 5,235,992 | A | 8/1993 | Sensabaugh |
| 5,243,999 | A | 9/1993 | Smith |
| 5,246,018 | A | 9/1993 | Deevi et al. |
| 5,249,586 | A | 10/1993 | Morgan et al. |
| 5,261,424 | A | 11/1993 | Sprinkel, Jr. |
| 5,269,327 | A | 12/1993 | Counts et al. |
| 5,285,798 | A | 2/1994 | Banerjee et al. |
| 5,293,883 | A | 3/1994 | Edwards |
| 5,301,694 | A | 4/1994 | Raymond |
| 5,303,720 | A | 4/1994 | Banerjee et al. |
| 5,318,050 | A | 6/1994 | Gonzalez-Parra et al. |
| 5,322,075 | A | 6/1994 | Deevi et al. |
| 5,322,076 | A | 6/1994 | Brinkley et al. |
| 5,339,838 | A | 8/1994 | Young et al. |
| 5,345,951 | A | 9/1994 | Serrano et al. |
| 5,353,813 | A | 10/1994 | Deevi et al. |
| 5,357,984 | A | 10/1994 | Farrier et al. |
| 5,360,023 | A | 11/1994 | Blakley et al. |
| 5,369,723 | A | 11/1994 | Counts et al. |
| 5,372,148 | A | 12/1994 | McCafferty et al. |
| 5,377,698 | A | 1/1995 | Litzinger et al. |
| 5,388,574 | A | 2/1995 | Ingebrethsen et al. |
| 5,388,594 | A | 2/1995 | Counts et al. |
| 5,408,574 | A | 4/1995 | Deevi et al. |
| 5,435,186 | A | 7/1995 | Terhune et al. |
| 5,435,325 | A | 7/1995 | Clapp et al. |
| 5,445,169 | A | 8/1995 | Brinkley et al. |
| 5,468,266 | A | 11/1995 | Bensalem et al. |
| 5,468,936 | A | 11/1995 | Deevi et al. |
| 5,479,948 | A | 1/1996 | Counts et al. |
| 5,498,850 | A | 3/1996 | Das |
| 5,498,855 | A | 3/1996 | Deevi et al. |
| 5,499,636 | A | 3/1996 | Baggett, Jr. et al. |
| 5,501,237 | A | 3/1996 | Young et al. |
| 5,505,214 | A | 4/1996 | Collins et al. |
| 5,515,842 | A | 5/1996 | Ramseyer et al. |
| 5,530,225 | A | 6/1996 | Hajaligol |
| 5,551,450 | A | 9/1996 | Hemsley |
| 5,551,451 | A | 9/1996 | Riggs et al. |
| 5,564,442 | A | 10/1996 | MacDonald et al. |
| 5,573,692 | A | 11/1996 | Das et al. |
| 5,591,368 | A | 1/1997 | Fleischhauer et al. |
| 5,593,792 | A | 1/1997 | Farrier et al. |
| 5,595,577 | A | 1/1997 | Bensalem et al. |
| 5,596,706 | A | 1/1997 | Sikk et al. |
| 5,611,360 | A | 3/1997 | Tang |
| 5,613,504 | A | 3/1997 | Collins et al. |
| 5,613,505 | A | 3/1997 | Campbell et al. |
| 5,649,552 | A | 7/1997 | Cho et al. |
| 5,649,554 | A | 7/1997 | Sprinkel et al. |
| 5,659,656 | A | 8/1997 | Das |
| 5,665,262 | A | 9/1997 | Hajaligol et al. |
| 5,666,976 | A | 9/1997 | Adams et al. |
| 5,666,977 | A | 9/1997 | Higgins et al. |
| 5,666,978 | A | 9/1997 | Counts et al. |
| 5,687,746 | A | 11/1997 | Rose et al. |
| 5,692,525 | A | 12/1997 | Counts et al. |
| 5,692,526 | A | 12/1997 | Adams et al. |

(56) References Cited

U.S. PATENT DOCUMENTS

| | | | |
|---|---|---|---|
| 5,708,258 A | 1/1998 | Counts et al. | |
| 5,711,320 A | 1/1998 | Martin | |
| 5,726,421 A | 3/1998 | Fleischhauer et al. | |
| 5,727,571 A | 3/1998 | Meiling et al. | |
| 5,730,158 A | 3/1998 | Collins et al. | |
| 5,750,964 A | 5/1998 | Counts et al. | |
| 5,799,663 A | 9/1998 | Gross et al. | |
| 5,816,263 A | 10/1998 | Counts et al. | |
| 5,819,756 A | 10/1998 | Mielordt | |
| 5,829,453 A | 11/1998 | White et al. | |
| 5,865,185 A | 2/1999 | Collins et al. | |
| 5,865,186 A | 2/1999 | Volsey, II | |
| 5,878,752 A | 3/1999 | Adams et al. | |
| 5,880,439 A | 3/1999 | Deevi et al. | |
| 5,894,841 A | 4/1999 | Voges | |
| 5,915,387 A | 7/1999 | Baggett, Jr. et al. | |
| 5,934,289 A | 8/1999 | Watkins et al. | |
| 5,954,979 A | 9/1999 | Counts et al. | |
| 5,967,148 A | 10/1999 | Harris et al. | |
| 6,026,820 A | 2/2000 | Baggett, Jr. et al. | |
| 6,033,623 A | 3/2000 | Deevi et al. | |
| 6,040,560 A | 3/2000 | Fleischhauer et al. | |
| 6,053,176 A | 4/2000 | Adams et al. | |
| 6,089,857 A | 7/2000 | Matsuura et al. | |
| 6,095,153 A | 8/2000 | Kessler et al. | |
| 6,116,247 A | 9/2000 | Banyasz et al. | |
| 6,119,700 A | 9/2000 | Fleischhauer et al. | |
| 6,125,853 A | 10/2000 | Susa et al. | |
| 6,125,855 A | 10/2000 | Nevett et al. | |
| 6,125,866 A | 10/2000 | Nichols et al. | |
| 6,155,268 A | 12/2000 | Takeuchi | |
| 6,164,287 A | 12/2000 | White | |
| 6,182,670 B1 | 2/2001 | White | |
| 6,196,218 B1 | 3/2001 | Voges | |
| 6,196,219 B1 | 3/2001 | Hess et al. | |
| 6,216,706 B1 | 4/2001 | Kumar et al. | |
| 6,289,898 B1 | 9/2001 | Fournier et al. | |
| 6,349,729 B1 | 2/2002 | Pham | |
| 6,357,671 B1 | 3/2002 | Cewers | |
| 6,418,938 B1 | 7/2002 | Fleischhauer et al. | |
| 6,446,426 B1 | 8/2002 | Sweeney et al. | |
| 6,532,965 B1 | 3/2003 | Abhulimen et al. | |
| 6,598,607 B2 | 7/2003 | Adiga et al. | |
| 6,601,776 B1 | 8/2003 | Oljaca et al. | |
| 6,615,840 B1 | 9/2003 | Fournier et al. | |
| 6,688,313 B2 | 2/2004 | Wrenn et al. | |
| 6,701,936 B2 | 3/2004 | Shafer et al. | |
| 6,715,494 B1 | 4/2004 | McCoy | |
| 6,730,832 B1 | 5/2004 | Dominguez et al. | |
| 6,772,756 B2 | 8/2004 | Shayan | |
| 6,803,545 B2 | 10/2004 | Blake et al. | |
| 6,803,550 B2 | 10/2004 | Sharpe et al. | |
| 6,810,883 B2 | 11/2004 | Felter et al. | |
| 6,854,461 B2 | 2/2005 | Nichols | |
| 6,854,470 B1 | 2/2005 | Pu | |
| 6,994,096 B2 | 2/2006 | Rostami et al. | |
| 7,011,096 B2 | 3/2006 | Li et al. | |
| 7,017,585 B2 | 3/2006 | Li et al. | |
| 7,025,066 B2 | 4/2006 | Lawson et al. | |
| 7,117,867 B2 | 10/2006 | Cox et al. | |
| 7,163,015 B2 | 1/2007 | Moffitt | |
| 7,173,322 B2 | 2/2007 | Cox et al. | |
| 7,185,659 B2 | 3/2007 | Sharpe et al. | |
| 7,234,470 B2 | 6/2007 | Yang | |
| 7,290,549 B2 | 11/2007 | Banerjee et al. | |
| 7,293,565 B2 | 11/2007 | Griffin et al. | |
| 7,392,809 B2 | 7/2008 | Larson et al. | |
| 7,513,253 B2 | 4/2009 | Kobayashi et al. | |
| 7,647,932 B2 | 1/2010 | Cantrell et al. | |
| 7,690,385 B2 | 4/2010 | Moffitt | |
| 7,692,123 B2 | 4/2010 | Baba et al. | |
| 7,726,320 B2 | 6/2010 | Robinson et al. | |
| 7,775,459 B2 | 8/2010 | Martens, III et al. | |
| 7,810,505 B2 | 10/2010 | Yang | |
| 7,832,410 B2 | 11/2010 | Hon | |
| 7,845,359 B2 | 12/2010 | Montaser | |
| 7,878,209 B2 | 2/2011 | Newbery et al. | |
| 7,896,006 B2 | 3/2011 | Hamano et al. | |
| 7,918,109 B2 | 4/2011 | Pinkowski et al. | |
| 8,066,010 B2 | 11/2011 | Newbery et al. | |
| 8,079,371 B2 | 12/2011 | Robinson et al. | |
| 8,127,772 B2 | 3/2012 | Montaser | |
| 8,156,944 B2 | 4/2012 | Han | |
| 8,314,591 B2 | 11/2012 | Terry et al. | |
| 8,365,742 B2 | 2/2013 | Hon | |
| 8,375,957 B2 | 2/2013 | Hon | |
| 8,393,331 B2 | 3/2013 | Hon | |
| 8,402,976 B2 | 3/2013 | Fernando et al. | |
| 8,499,766 B1 | 8/2013 | Newton | |
| 8,528,569 B1 | 9/2013 | Newton | |
| 8,550,069 B2 | 10/2013 | Alelov | |
| 8,559,800 B2 | 10/2013 | Ellis et al. | |
| 8,794,231 B2 | 8/2014 | Thorens et al. | |
| 8,851,081 B2 | 10/2014 | Fernando et al. | |
| 8,997,753 B2 | 4/2015 | Li et al. | |
| 9,277,770 B2 * | 3/2016 | DePiano | A24F 47/008 |
| 2002/0146242 A1 | 10/2002 | Vieira | |
| 2003/0131859 A1 | 7/2003 | Li et al. | |
| 2003/0226837 A1 | 12/2003 | Blake et al. | |
| 2004/0020500 A1 | 2/2004 | Wrenn et al. | |
| 2004/0118401 A1 | 6/2004 | Smith et al. | |
| 2004/0129280 A1 | 7/2004 | Woodson et al. | |
| 2004/0149296 A1 | 8/2004 | Rostami et al. | |
| 2004/0200488 A1 | 10/2004 | Felter et al. | |
| 2004/0226568 A1 | 11/2004 | Takeuchi et al. | |
| 2004/0255965 A1 | 12/2004 | Perfetti et al. | |
| 2005/0016549 A1 | 1/2005 | Banerjee et al. | |
| 2005/0016550 A1 | 1/2005 | Katase | |
| 2005/0066986 A1 | 3/2005 | Nestor et al. | |
| 2005/0172976 A1 | 8/2005 | Newman et al. | |
| 2005/0274390 A1 | 12/2005 | Banerjee et al. | |
| 2006/0016453 A1 | 1/2006 | Kim | |
| 2006/0057527 A1 | 3/2006 | Adair et al. | |
| 2006/0070633 A1 | 4/2006 | Rostami et al. | |
| 2006/0162733 A1 | 7/2006 | McGrath et al. | |
| 2006/0185687 A1 | 8/2006 | Hearn et al. | |
| 2006/0196518 A1 | 9/2006 | Hon | |
| 2007/0074734 A1 | 4/2007 | Braunshteyn et al. | |
| 2007/0102013 A1 | 5/2007 | Adams et al. | |
| 2007/0215167 A1 | 9/2007 | Crooks et al. | |
| 2007/0283972 A1 | 12/2007 | Monsees et al. | |
| 2008/0085103 A1 | 4/2008 | Beland et al. | |
| 2008/0092912 A1 | 4/2008 | Robinson et al. | |
| 2008/0149118 A1 | 6/2008 | Oglesby et al. | |
| 2008/0245377 A1 | 10/2008 | Marshall et al. | |
| 2008/0257367 A1 | 10/2008 | Paterno et al. | |
| 2008/0276947 A1 | 11/2008 | Martzel | |
| 2008/0302374 A1 | 12/2008 | Wengert et al. | |
| 2009/0056389 A1 | 3/2009 | Pinkowski et al. | |
| 2009/0065010 A1 | 3/2009 | Shands | |
| 2009/0071831 A1 | 3/2009 | Chen et al. | |
| 2009/0095311 A1 | 4/2009 | Hon | |
| 2009/0095312 A1 | 4/2009 | Herbrich et al. | |
| 2009/0126745 A1 | 5/2009 | Hon | |
| 2009/0188490 A1 | 7/2009 | Hon | |
| 2009/0230117 A1 | 9/2009 | Fernando et al. | |
| 2009/0238547 A1 | 9/2009 | Borgmeier | |
| 2009/0260641 A1 | 10/2009 | Monsees et al. | |
| 2009/0260642 A1 | 10/2009 | Monsees et al. | |
| 2009/0272379 A1 | 11/2009 | Thorens et al. | |
| 2009/0283103 A1 | 11/2009 | Nielsen et al. | |
| 2009/0293892 A1 | 12/2009 | Williams et al. | |
| 2009/0320863 A1 | 12/2009 | Fernando et al. | |
| 2009/0324206 A1 | 12/2009 | Young et al. | |
| 2010/0006113 A1 | 1/2010 | Urtsev et al. | |
| 2010/0024834 A1 | 2/2010 | Oglesby et al. | |
| 2010/0043809 A1 | 2/2010 | Magnon | |
| 2010/0059070 A1 | 3/2010 | Potter et al. | |
| 2010/0059073 A1 | 3/2010 | Hoffmann et al. | |
| 2010/0065075 A1 | 3/2010 | Banerjee et al. | |
| 2010/0083959 A1 | 4/2010 | Siller | |
| 2010/0163063 A1 | 7/2010 | Fernando et al. | |
| 2010/0200006 A1 | 8/2010 | Robinson et al. | |
| 2010/0229881 A1 | 9/2010 | Hearn | |

(56) References Cited

U.S. PATENT DOCUMENTS

| | | | |
|---|---|---|---|
| 2010/0242974 | A1 | 9/2010 | Pan |
| 2010/0242976 | A1 | 9/2010 | Katayama et al. |
| 2010/0258139 | A1 | 10/2010 | Onishi et al. |
| 2010/0300467 | A1 | 12/2010 | Kuistilla et al. |
| 2010/0307518 | A1 | 12/2010 | Wang |
| 2010/0313901 | A1 | 12/2010 | Fernando et al. |
| 2011/0005535 | A1 | 1/2011 | Xiu |
| 2011/0011396 | A1 | 1/2011 | Fang |
| 2011/0036363 | A1 | 2/2011 | Urtsev et al. |
| 2011/0036365 | A1 | 2/2011 | Chong et al. |
| 2011/0073121 | A1 | 3/2011 | Levin et al. |
| 2011/0088707 | A1 | 4/2011 | Hajaligol |
| 2011/0094523 | A1 | 4/2011 | Thorens et al. |
| 2011/0120480 | A1 | 5/2011 | Brenneise |
| 2011/0126847 | A1 | 6/2011 | Zuber et al. |
| 2011/0126848 | A1 | 6/2011 | Zuber et al. |
| 2011/0155153 | A1 | 6/2011 | Thorens et al. |
| 2011/0155718 | A1 | 6/2011 | Greim et al. |
| 2011/0162663 | A1 | 7/2011 | Bryman |
| 2011/0168194 | A1 | 7/2011 | Hon |
| 2011/0180082 | A1 | 7/2011 | Banerjee et al. |
| 2011/0218622 | A1 | 9/2011 | Shaolian et al. |
| 2011/0232654 | A1 | 9/2011 | Mass |
| 2011/0265806 | A1 | 11/2011 | Alarcon et al. |
| 2011/0303231 | A1 | 12/2011 | Li et al. |
| 2011/0309157 | A1 | 12/2011 | Yang et al. |
| 2012/0042885 | A1 | 2/2012 | Stone et al. |
| 2012/0060853 | A1 | 3/2012 | Robinson et al. |
| 2012/0090630 | A1 | 4/2012 | Hon |
| 2012/0111347 | A1 | 5/2012 | Hon |
| 2012/0132643 | A1 | 5/2012 | Choi et al. |
| 2012/0145169 | A1 | 6/2012 | Wu |
| 2012/0227752 | A1 | 9/2012 | Alelov |
| 2012/0231464 | A1 | 9/2012 | Yu et al. |
| 2012/0260927 | A1 | 10/2012 | Liu |
| 2012/0279512 | A1 | 11/2012 | Hon |
| 2012/0318882 | A1 | 12/2012 | Abehasera |
| 2013/0037041 | A1 | 2/2013 | Worm et al. |
| 2013/0056013 | A1 | 3/2013 | Terry et al. |
| 2013/0081625 | A1 | 4/2013 | Rustad et al. |
| 2013/0081642 | A1 | 4/2013 | Safari |
| 2013/0094841 | A1 | 4/2013 | Garvey et al. |
| 2013/0168363 | A1 | 7/2013 | Arakawa |
| 2013/0192619 | A1 | 8/2013 | Tucker et al. |
| 2013/0199528 | A1 | 8/2013 | Goodman et al. |
| 2013/0306084 | A1 | 11/2013 | Flick |
| 2013/0313246 | A1 | 11/2013 | Long et al. |
| 2013/0319439 | A1 | 12/2013 | Gorelick et al. |
| 2013/0340750 | A1 | 12/2013 | Thorens et al. |
| 2013/0340775 | A1 | 12/2013 | Juster et al. |
| 2014/0060554 | A1 | 3/2014 | Collett et al. |
| 2014/0060555 | A1 | 3/2014 | Chang et al. |
| 2014/0096781 | A1 | 4/2014 | Sears et al. |
| 2014/0096782 | A1 | 4/2014 | Ampolini et al. |
| 2014/0190496 | A1 | 7/2014 | Wensley et al. |
| 2015/0007838 | A1 | 1/2015 | Fernando et al. |

FOREIGN PATENT DOCUMENTS

| | | | |
|---|---|---|---|
| CA | 2 752 255 | | 8/2010 |
| CN | 1541577 | | 11/2004 |
| CN | 2719043 | | 8/2005 |
| CN | 101084034 | | 12/2007 |
| CN | 200997909 | | 1/2008 |
| CN | 101116542 | | 2/2008 |
| CN | 101176805 | | 5/2008 |
| CN | 101606758 | | 12/2009 |
| CN | 201379072 | | 1/2010 |
| CN | 102356929 | | 2/2012 |
| CN | 202407080 | | 9/2012 |
| CN | 202738815 | | 2/2013 |
| CN | 102894485 | | 4/2015 |
| DE | 10 2006 004 484 | | 8/2007 |
| DE | 102006041042 | | 3/2008 |
| DE | 20 2009 010 400 | | 11/2009 |
| EP | 0 295 122 | | 12/1988 |
| EP | 0 430 566 | | 6/1991 |
| EP | 0 845 220 | | 6/1998 |
| EP | 1 618 803 | | 1/2006 |
| EP | 2 316 286 | | 5/2011 |
| EP | 1 996 037 | | 4/2012 |
| EP | 2 468 116 | | 6/2012 |
| EP | 1 993 388 | | 8/2012 |
| GB | 1444461 | | 7/1976 |
| GB | 2469850 | | 11/2010 |
| JP | 2012-517831 | | 8/2012 |
| RU | 94815 | U1 | 6/2010 |
| WO | WO 1986/02528 | | 5/1986 |
| WO | WO 1997/48293 | | 12/1997 |
| WO | WO 02/37990 | | 5/2002 |
| WO | WO 2003/034847 | | 5/2003 |
| WO | WO 2004/043175 | | 5/2004 |
| WO | WO 2005/099494 | | 10/2005 |
| WO | WO 2007/078273 | | 7/2007 |
| WO | WO 2007/131449 | | 11/2007 |
| WO | WO 2009/105919 | | 9/2009 |
| WO | WO 2009/155734 | | 12/2009 |
| WO | WO 2010/003480 | | 1/2010 |
| WO | WO 2010/045670 | | 4/2010 |
| WO | WO 2010/073122 | | 7/2010 |
| WO | WO 2010/091593 | | 8/2010 |
| WO | WO 2010/118644 | | 10/2010 |
| WO | WO 2010/140937 | | 12/2010 |
| WO | WO 2011/010334 | | 1/2011 |
| WO | WO 2011/081558 | | 7/2011 |
| WO | WO 2012/072762 | | 6/2012 |
| WO | WO 2012/100523 | | 8/2012 |
| WO | WO 2013/089551 | | 6/2013 |

OTHER PUBLICATIONS

U.S. Appl. No. 13/432,406, filed Mar. 28, 2012, Griffith, Jr.
U.S. Appl. No. 13/536,438, filed Jul. 28, 2012, Sebastian.
U.S. Appl. No. 13/602,871, filed Sep. 4, 2012, Collett.
U.S. Appl. No. 13/603,612, filed Sep. 5, 2012, Chang.
U.S. Appl. No. 13/647,000, filed Oct. 8, 2012, Sears.
U.S. Appl. No. 13/708,381, filed Dec. 7, 2012, Ward.
U.S. Appl. No. 13/754,324, filed Jan. 30, 2013, Sears.
U.S. Appl. No. 13/788,455, filed Mar. 7, 2013, Novak, III.
U.S. Appl. No. 13/796,725, filed Mar. 12, 2013, Potter.
U.S. Appl. No. 13/802,950, filed Mar. 14, 2013, Chapman.
U.S. Appl. No. 13/826,929, filed Mar. 14, 2013, Ampolini.
U.S. Appl. No. 13/837,542, filed Mar. 15, 2013, Ampolini.
U.S. Appl. No. 13/840,264, filed Mar. 15, 2013, Novak, III.
U.S. Appl. No. 13/841,233, filed Mar. 15, 2013, DePiano.
U.S. Appl. No. 13/842,125, filed Mar. 15, 2013, DePiano.
Chinese Office Action dated Feb. 16, 2017 in Chinese application No. 201480024265.3.

* cited by examiner

ATOMIZER FOR AN AEROSOL DELIVERY DEVICE FORMED FROM A CONTINUOUSLY EXTENDING WIRE AND RELATED INPUT, CARTRIDGE, AND METHOD

CROSS-REFERENCE TO RELATED APPLICATIONS

This application is a continuation of U.S. pat. application Ser. No. 13/827,994, filed Mar. 14, 2013, which is incorporated herein by reference in its entirety.

FIELD OF THE DISCLOSURE

The present disclosure relates to atomizers for aerosol delivery devices such as smoking articles, and more particularly to atomizers comprising a wire and a liquid transport element. The atomizers may be configured to heat a material, which may be made or derived from tobacco or otherwise incorporate tobacco, to form an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. patent application Ser. No. 13/432,406, filed Mar. 28, 2012, U.S. patent application Ser. No. 13/536,438, filed Jun. 28, 2012, U.S. patent application Ser. No. 13/602,871, filed Sep. 4, 2012, and U.S. patent application Ser. No. 13/647,000, filed Oct. 8, 2012, which are incorporated herein by reference.

Certain tobacco products that have employed electrical energy to produce heat for smoke or aerosol formation, and in particular, certain products that have been referred to as electronic cigarette products, have been commercially available throughout the world. Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; COHITA™, COLIBRI™, ELITE CLASSIC™, MAGNUM™, PHANTOM™ and SENSE™ by Epuffer® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; GREEN SMOKE® by Green Smoke Inc. USA; GREENARETTE™ by Greenarette LLC; HALLIGAN™, HENDU™, JET™, MAXXQ™ PINK™ and PITBULL™ by Smoke Stik®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC and VUSE® by R. J. Reynolds Vapor Company. Yet other electrically powered aerosol delivery devices, and in particular those devices that have been characterized as so-called electronic cigarettes, have been marketed under the tradenames BLU™; COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP® and SOUTH BEACH SMOKE™.

It would be desirable to provide a smoking article that employs heat produced by electrical energy to provide the sensations of cigarette, cigar, or pipe smoking, that does so without combusting tobacco to any significant degree, that does so without the need of a combustion heat source, and that does so without necessarily delivering considerable quantities of incomplete combustion and pyrolysis products. Further, advances with respect to manufacturing electronic smoking articles would be desirable.

BRIEF SUMMARY OF THE DISCLOSURE

The present disclosure relates to aerosol delivery devices configured to produce aerosol. In one aspect an input for production of a plurality of atomizers is provided. The input may comprise a liquid transport element and a wire continuously extending along a longitudinal length of the liquid transport element and defining a plurality of heating elements. The heating elements may respectively comprise a plurality of coils of the wire.

In some embodiments the wire may be continuously wound about the liquid transport element. The wire may further define a plurality of end portions defining a first pitch. Each of the heating elements may comprise a plurality of contact portions positioned between the end portions and defining a second pitch and a heating portion positioned between the contact portions and defining a third pitch. The second pitch may be less than the first pitch, and the third pitch may be less than the first pitch and greater than the second pitch. Further, the second pitch may be substantially equal to a diameter of the wire.

In an additional aspect, an atomizer for an aerosol delivery device is provided. The atomizer may comprise a liquid transport element extending between a first liquid transport element end and a second liquid transport element end and a wire continuously extending along the liquid transport element from the first liquid transport element end to the second liquid transport element end and defining a heating element comprising a plurality of coils of the wire.

In some embodiments the wire may be continuously wound about the liquid transport element. The wire may further define a plurality of end portions defining a first pitch, and the heating element may comprise a plurality of contact portions positioned between the end portions and defining a second pitch and a heating portion positioned between the contact portions and defining a third pitch. The second pitch may be less than the first pitch, and the third pitch may be less than the first pitch and greater than the second pitch. The second pitch may be substantially equal to a diameter of the wire. The atomizer may further comprise a first heater terminal and a second heater terminal, and the contact portions of the heating element may respectively contact one of the first heater terminal and the second heater terminal. The end portions may respectively contact one of the first heater terminal and the second heater terminal.

In an additional aspect a cartridge for an aerosol delivery device is provided. The cartridge may comprise a base defining a connector end configured to engage a control body. Further, the cartridge may include a reservoir substrate configured to hold an aerosol precursor composition. The reservoir substrate may define a cavity extending therethrough from a first reservoir end to a second reservoir end, and the first reservoir end may be positioned proximate the base. The cartridge may additionally include an atomizer extending through the cavity of the reservoir substrate. The atomizer may comprise a liquid transport element extending between a first liquid transport element end and a second liquid transport element end and a wire continuously extending along the liquid transport element from the first liquid transport element end to the second liquid transport element end and defining a heating element comprising a plurality of coils of the wire.

In some embodiments the wire may be continuously wound about the liquid transport element. The wire may further define a plurality of end portions defining a first pitch, and the heating element may comprise a plurality of contact portions positioned between the end portions and defining a second pitch and a heating portion positioned between the contact portions and defining a third pitch. The second pitch may be less than the first pitch, and the third pitch may be less than the first pitch and greater than the second pitch. The second pitch may be substantially equal to a diameter of the wire.

In some embodiments the atomizer may further comprise a first heater terminal and a second heater terminal. The contact portions of the heating element may respectively contact one of the first heater terminal and the second heater terminal. The end portions may also respectively contact one of the first heater terminal and the second heater terminal. The reservoir substrate may define a plurality of grooves at the cavity extending between the first reservoir end and the second reservoir end and configured to receive the liquid transport element and the end portions.

In an additional aspect, a method of forming atomizers is provided. The method may comprise providing a liquid transport element, providing a wire, and coupling the wire to the liquid transport element such that the wire extends continuously along a longitudinal length of the liquid transport element and defines a plurality of heating elements. The heating elements may respectively comprise a plurality of coils of the wire.

In some embodiments coupling the wire to the liquid transport element may comprise continuously winding the wire about the liquid transport element. Winding the wire about the liquid transport element may comprise winding the wire to define a plurality of end portions defining a first pitch and winding the wire such that each of the heating elements comprises a plurality of contact portions positioned between the end portions and defining a second pitch and a heating portion positioned between the contact portions and defining a third pitch. The second pitch may be less than the first pitch, and the third pitch may be less than the first pitch and greater than the second pitch. In some embodiments the second pitch may be substantially equal to a diameter of the wire.

The method may further comprise cutting the liquid transport element and the wire at one of the end portions to separate one of the heating elements and a segment of the liquid transport element therefrom. Further, the method may include providing a first heater terminal and a second heater terminal and respectively engaging the contact portions of the one of the heating elements with the first heater terminal and the second heater terminal. The method may additionally include bending the one of the heating elements and the segment of the liquid transport element about the first heater terminal and the second heater terminal. The method may also include respectively engaging the end portions with one of the first heater terminal and the second heater terminal.

BRIEF DESCRIPTION OF THE FIGURES

Figure 1:
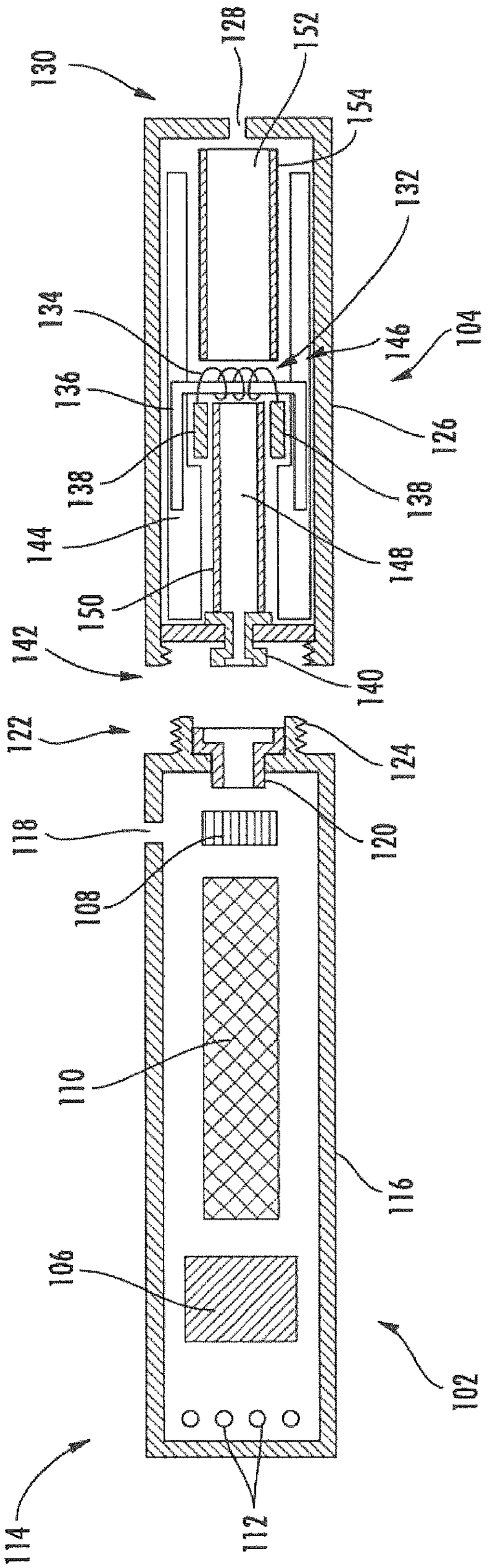
Figure 2:
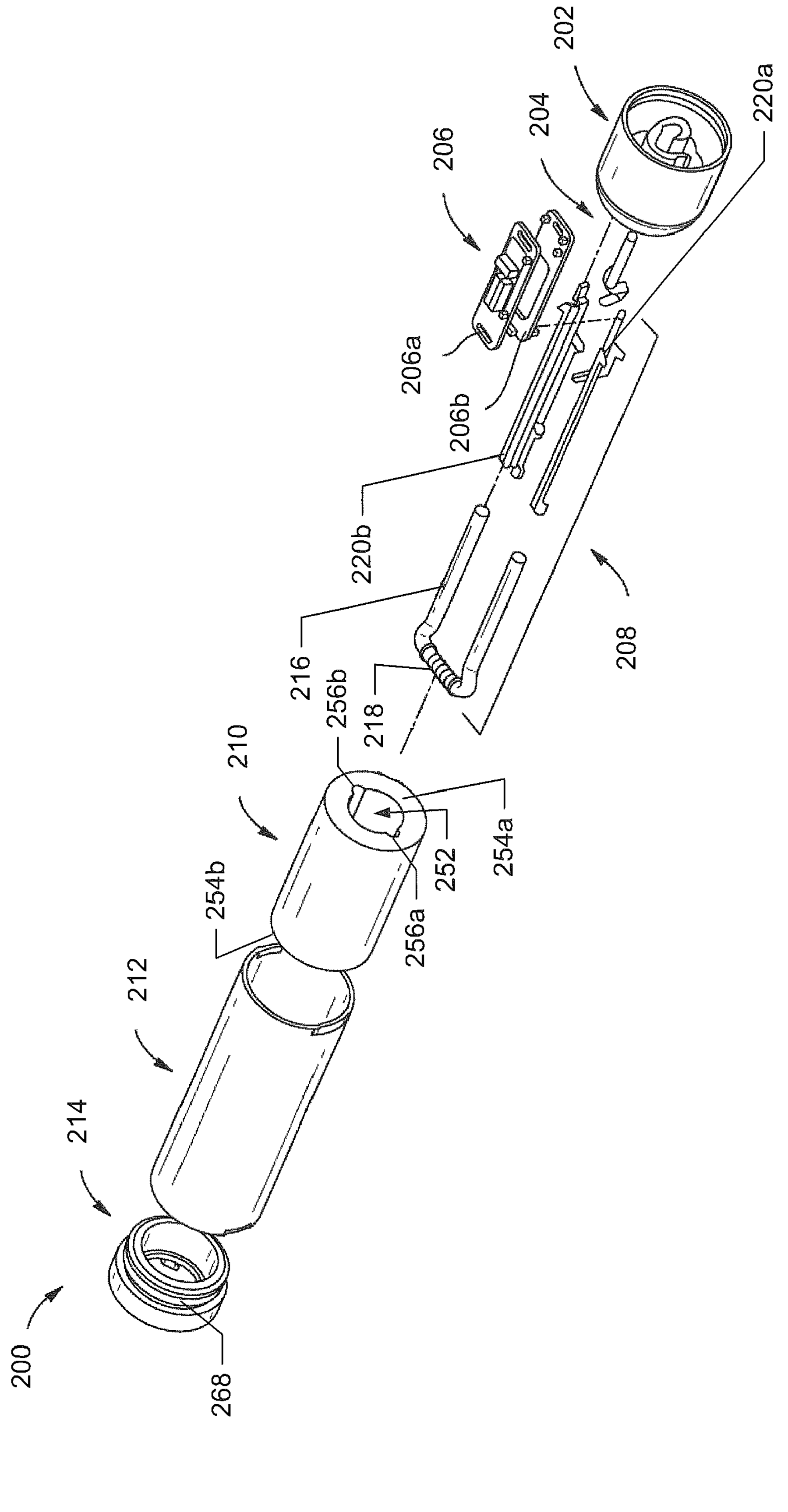
Figure 3:
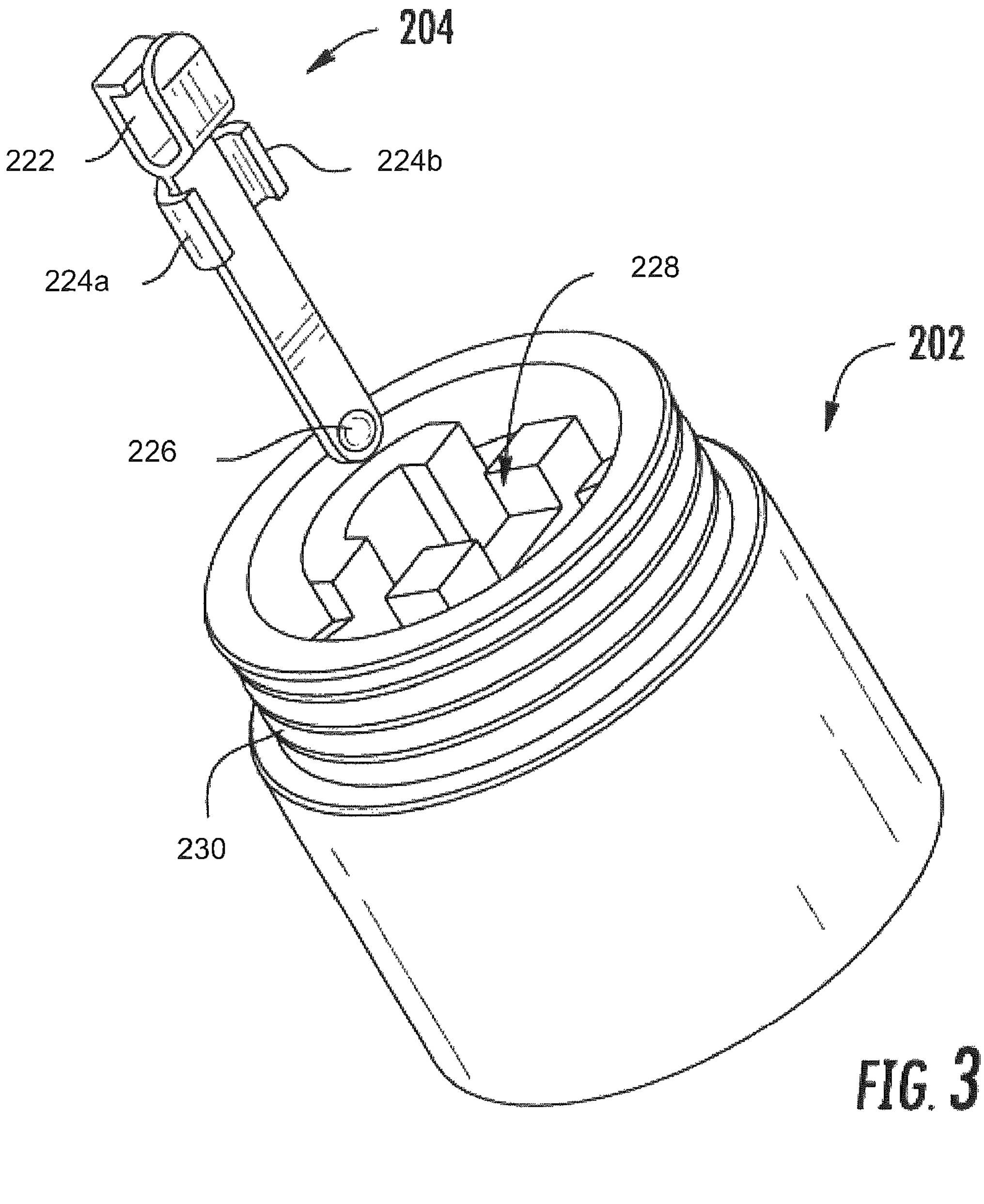
Figure 4:
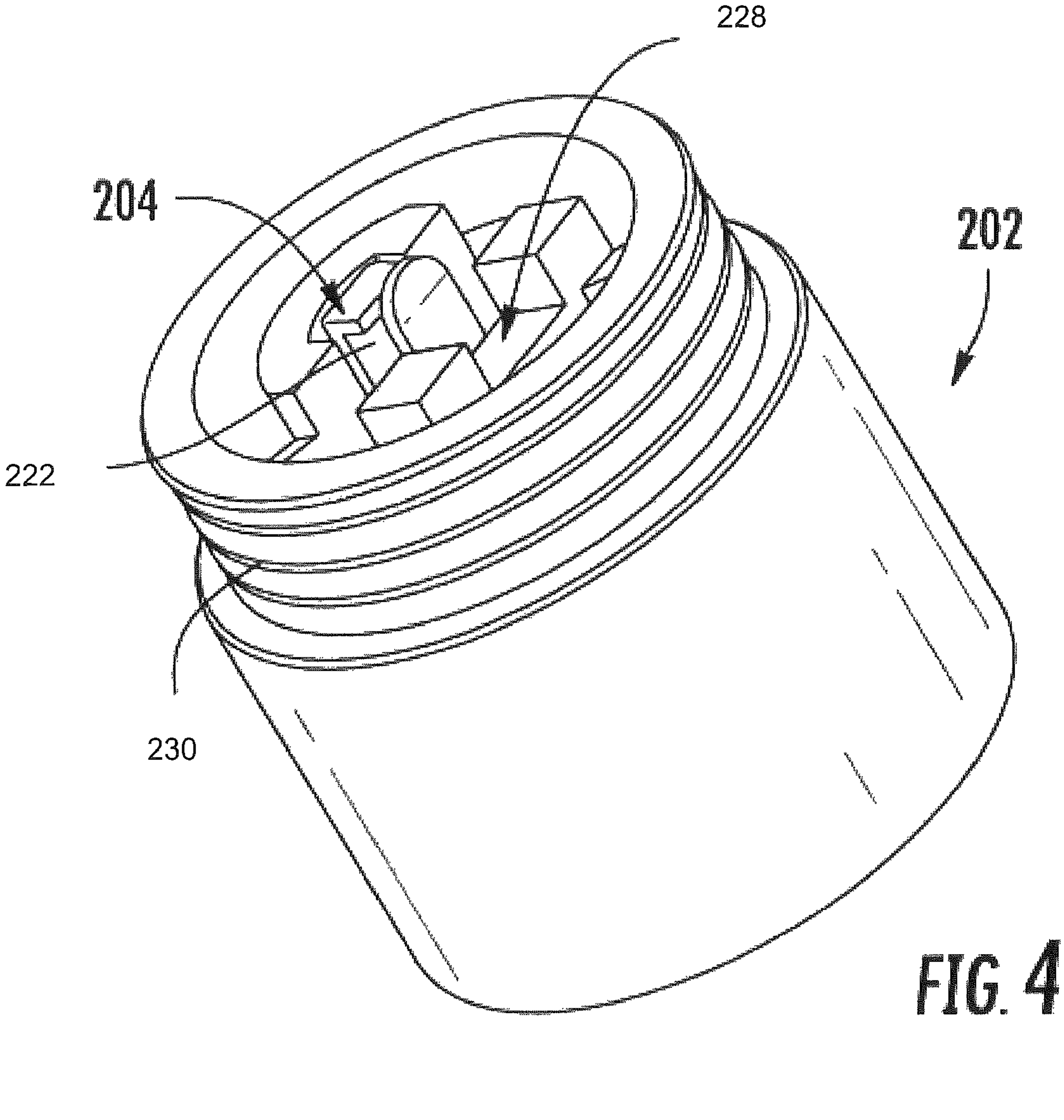
Figure 5:
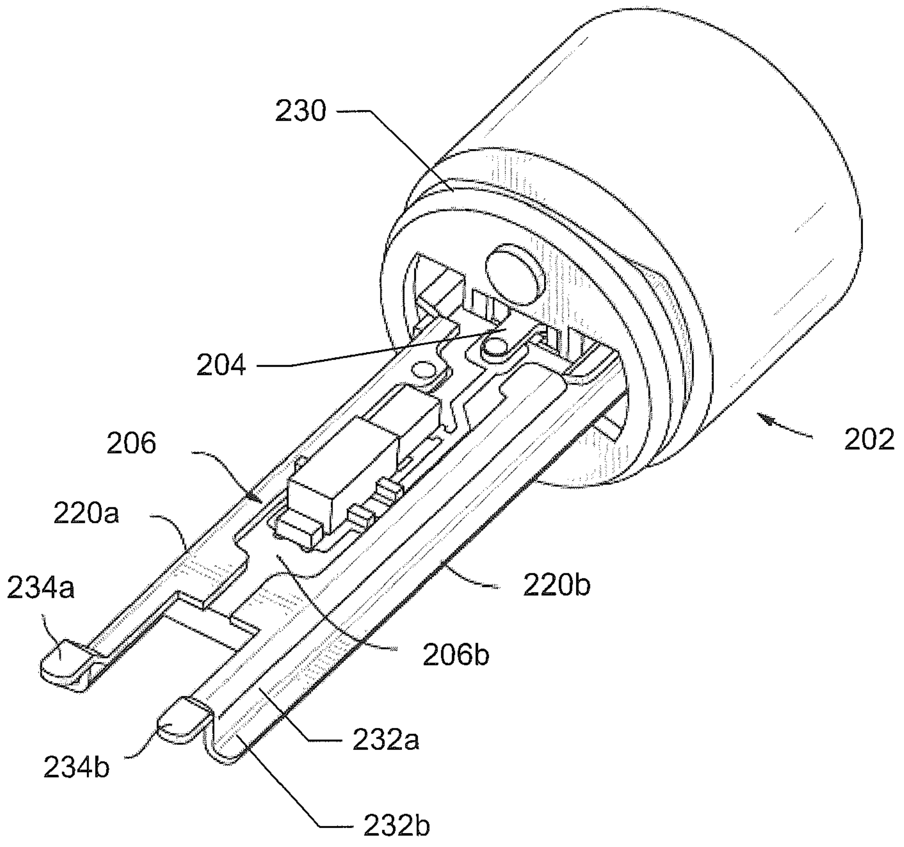
Figure 6:
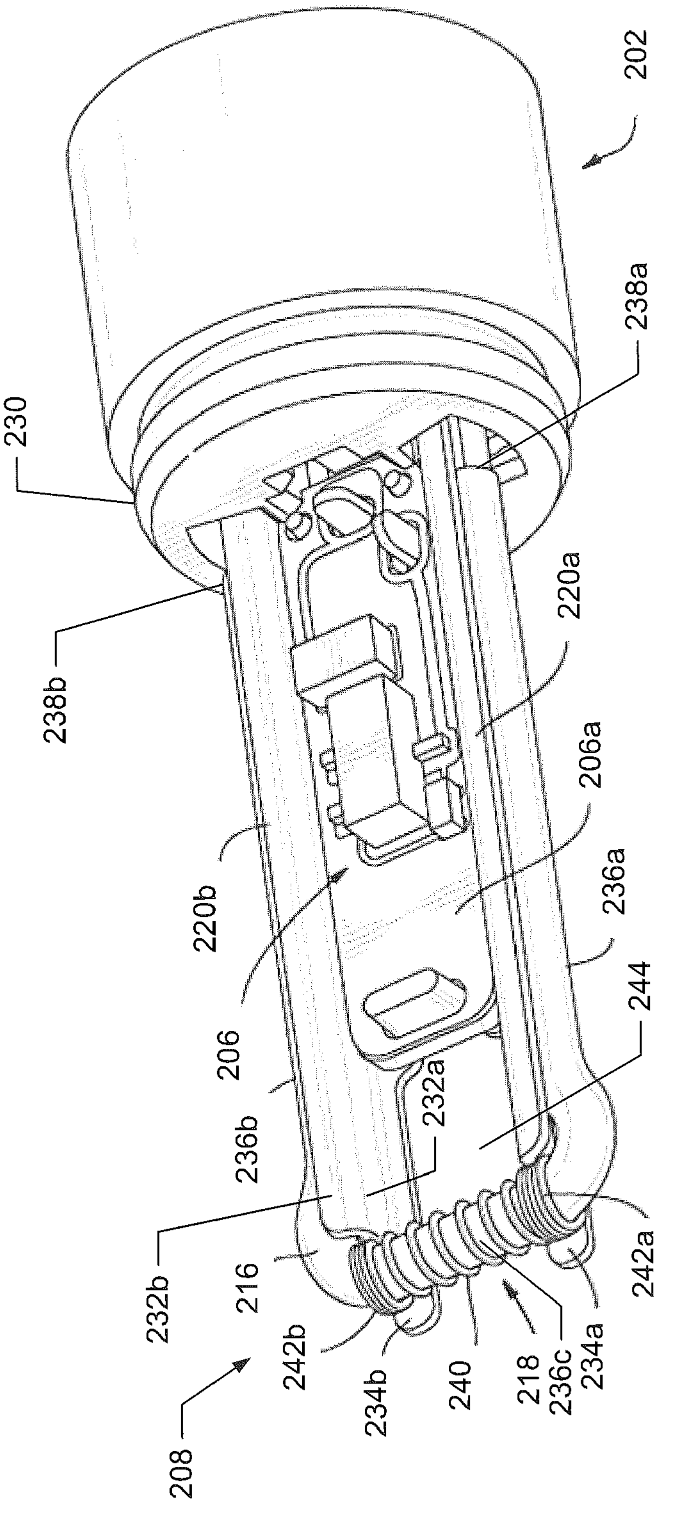
Figure 7:
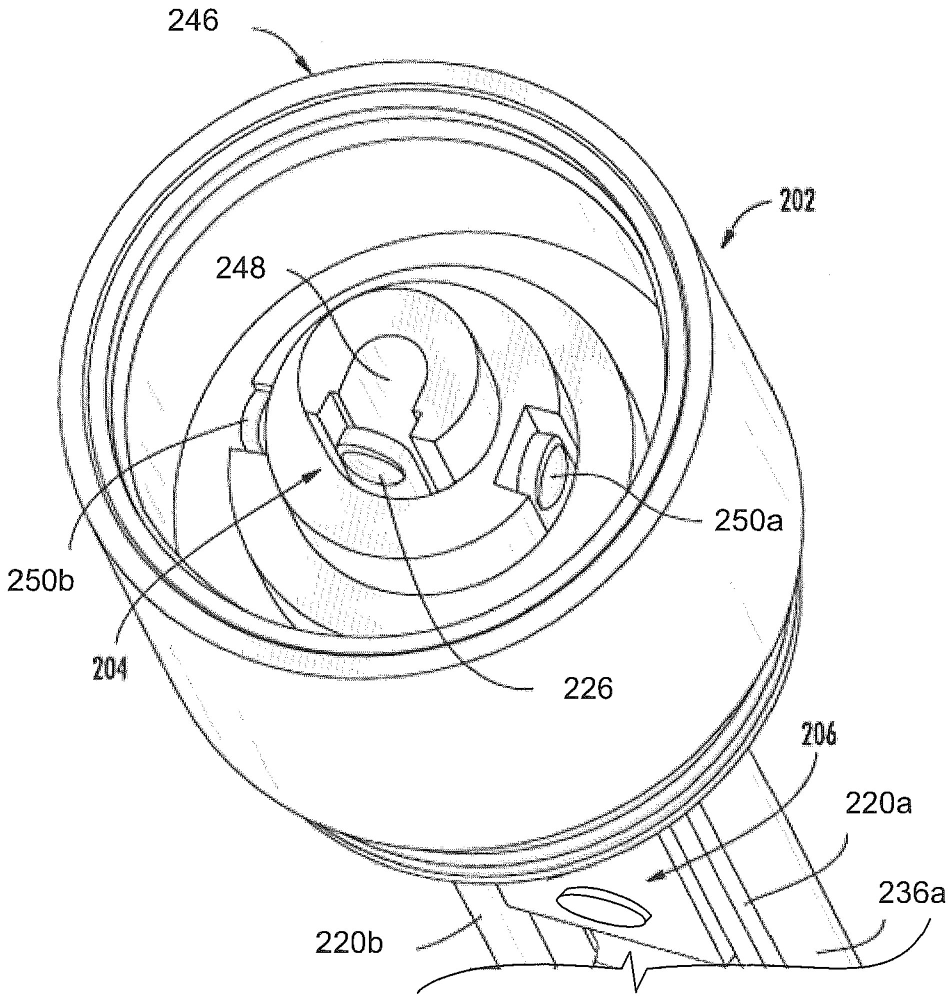
Figure 8:
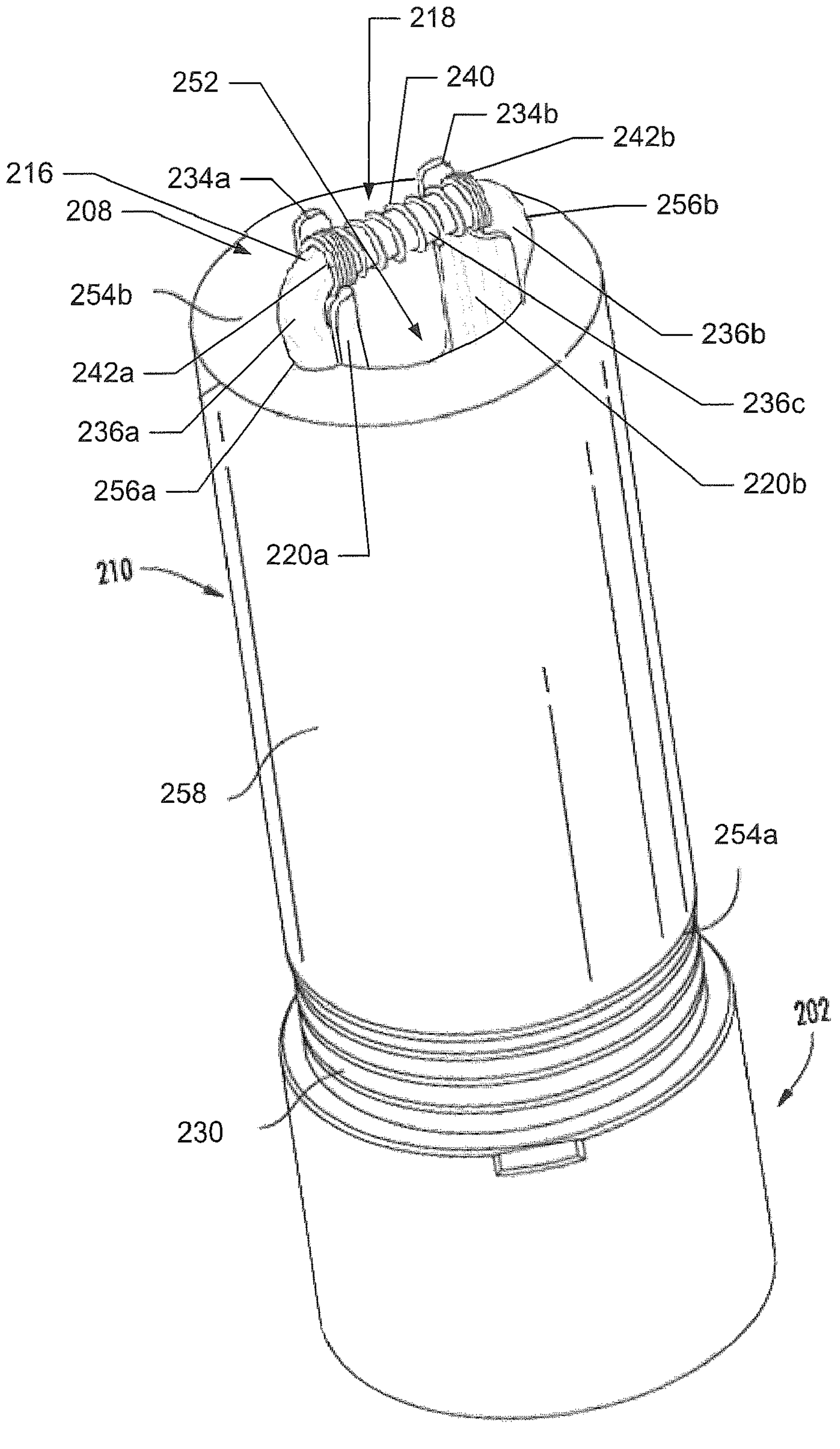
Figure 9:
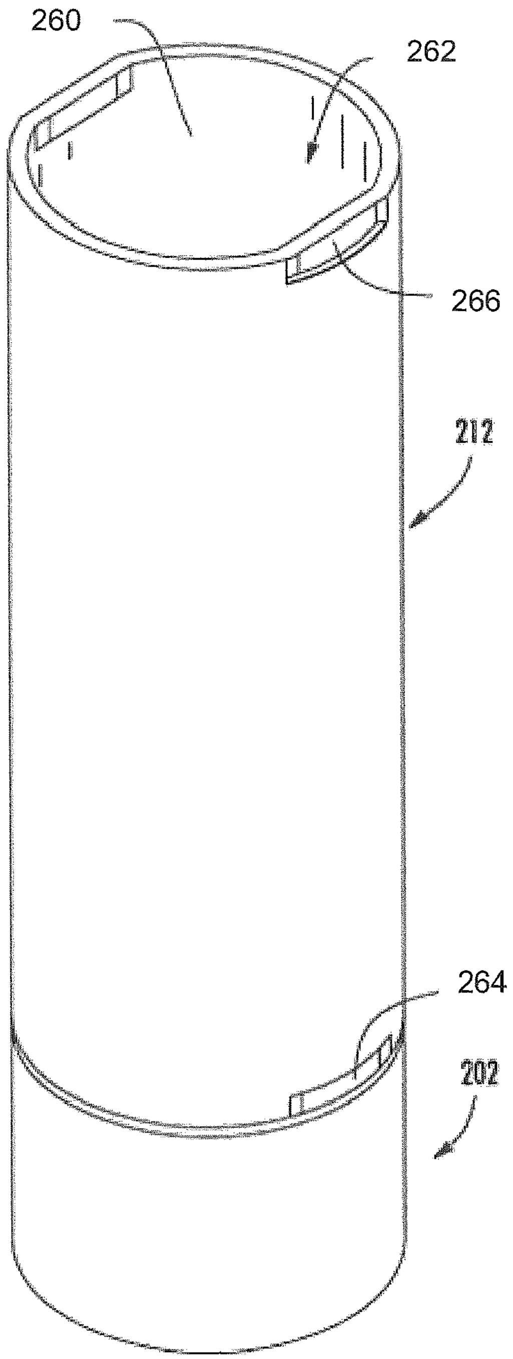
Figure 10:
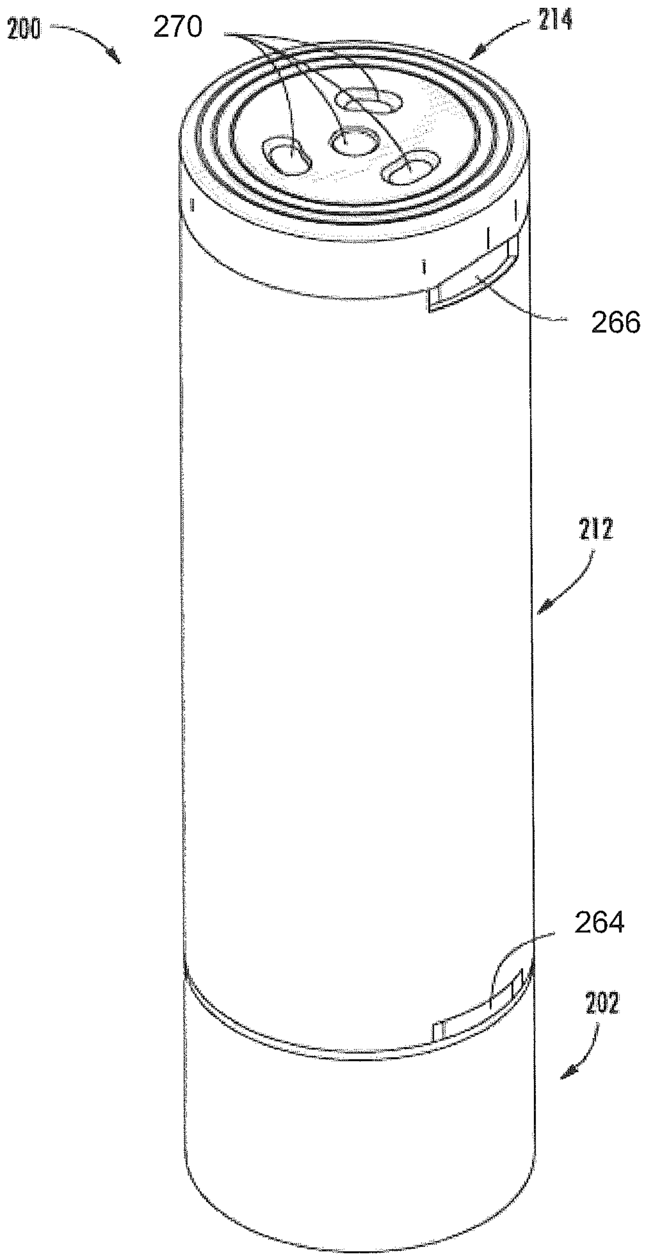
Figure 11:
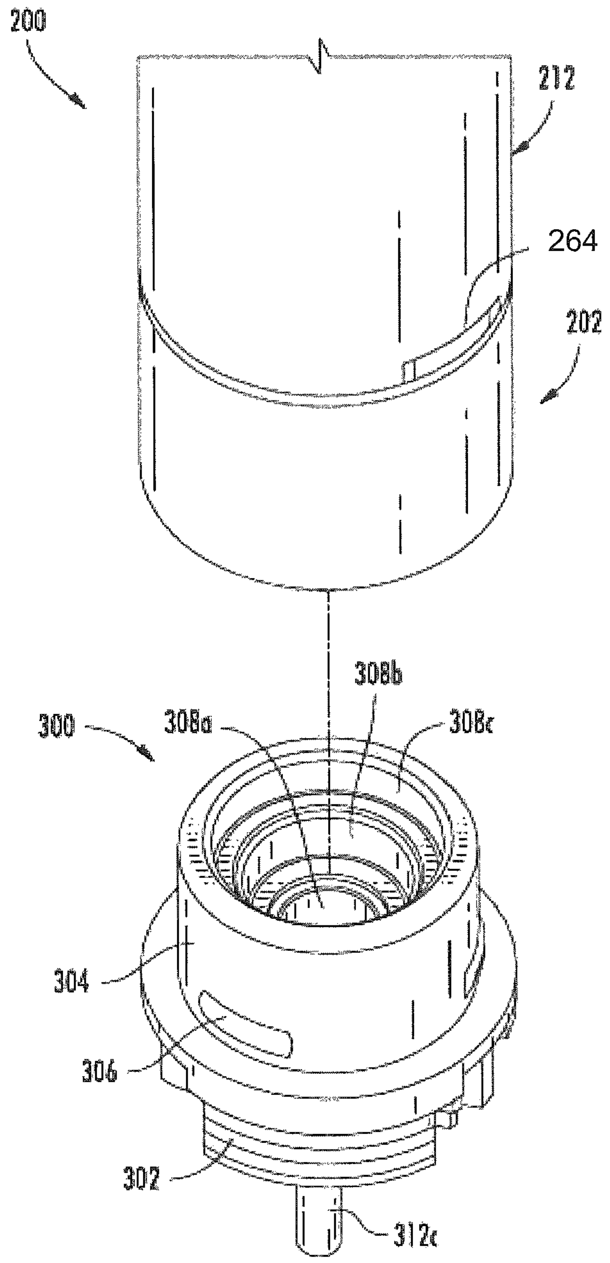
Figure 12:
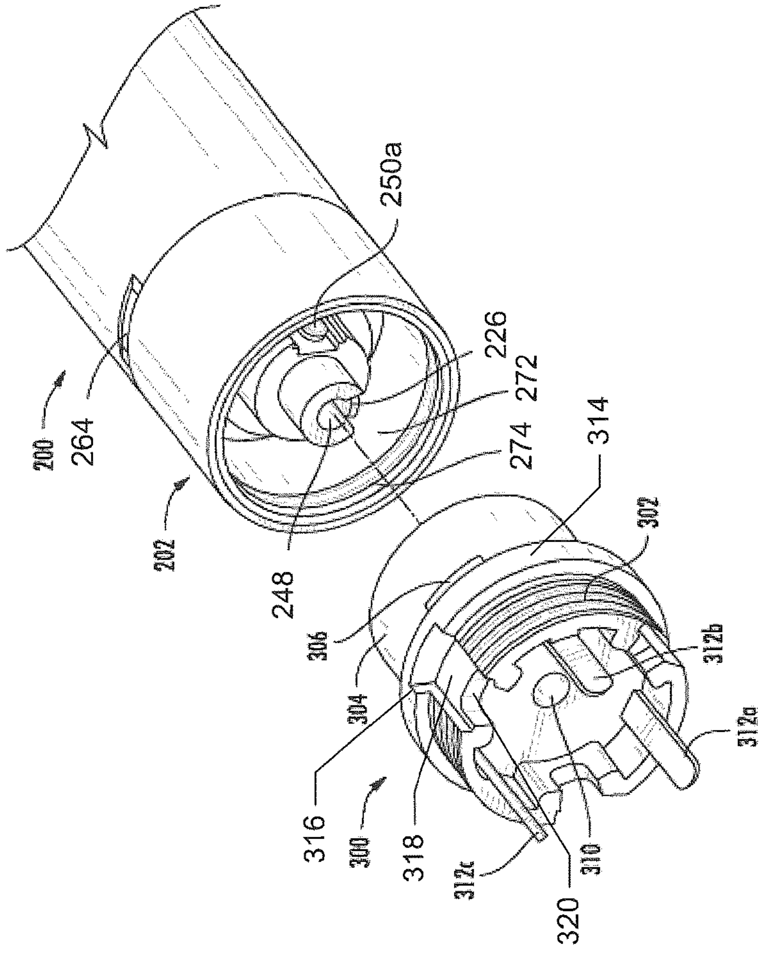
Figure 13:
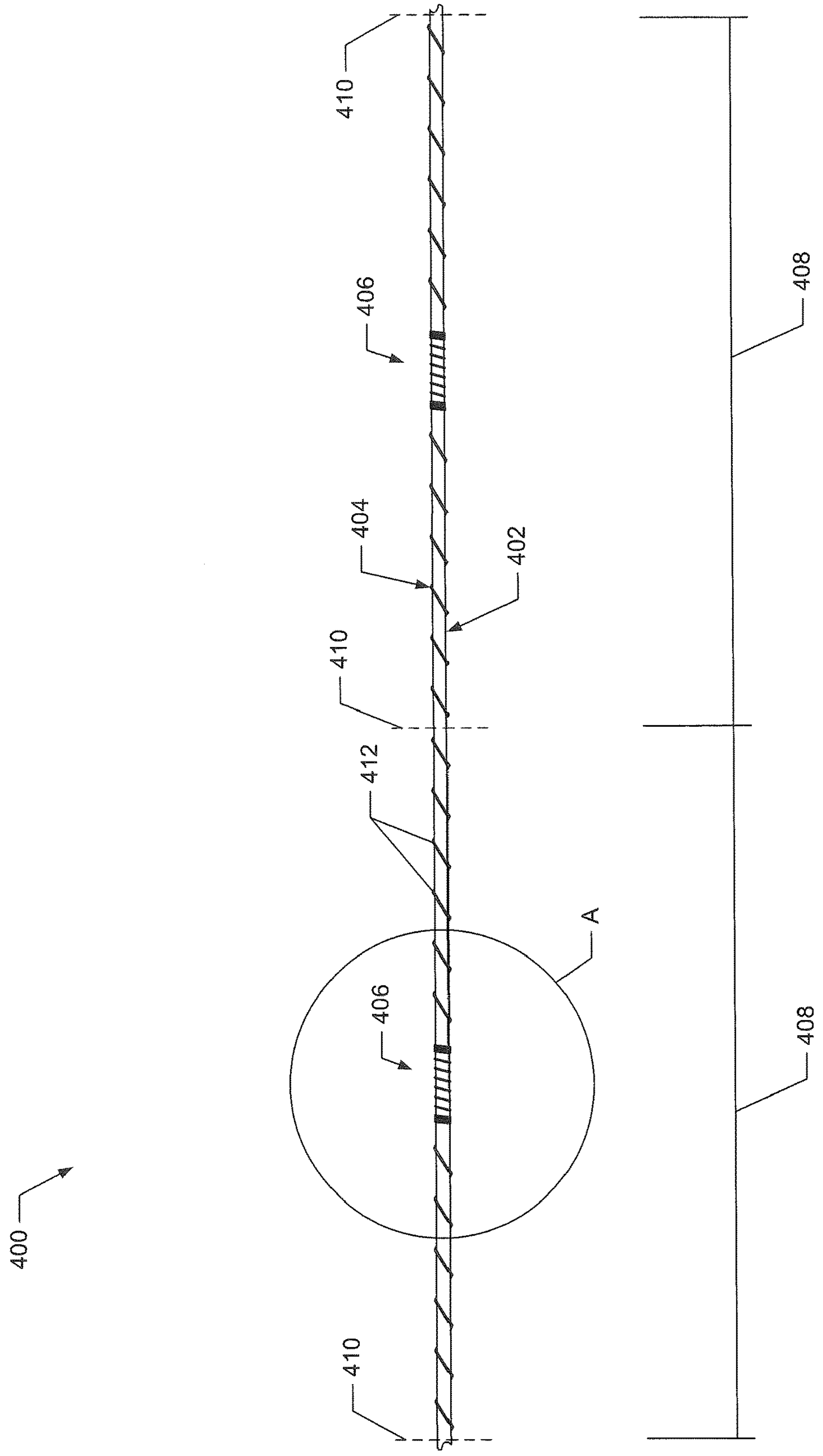
Figure 14:
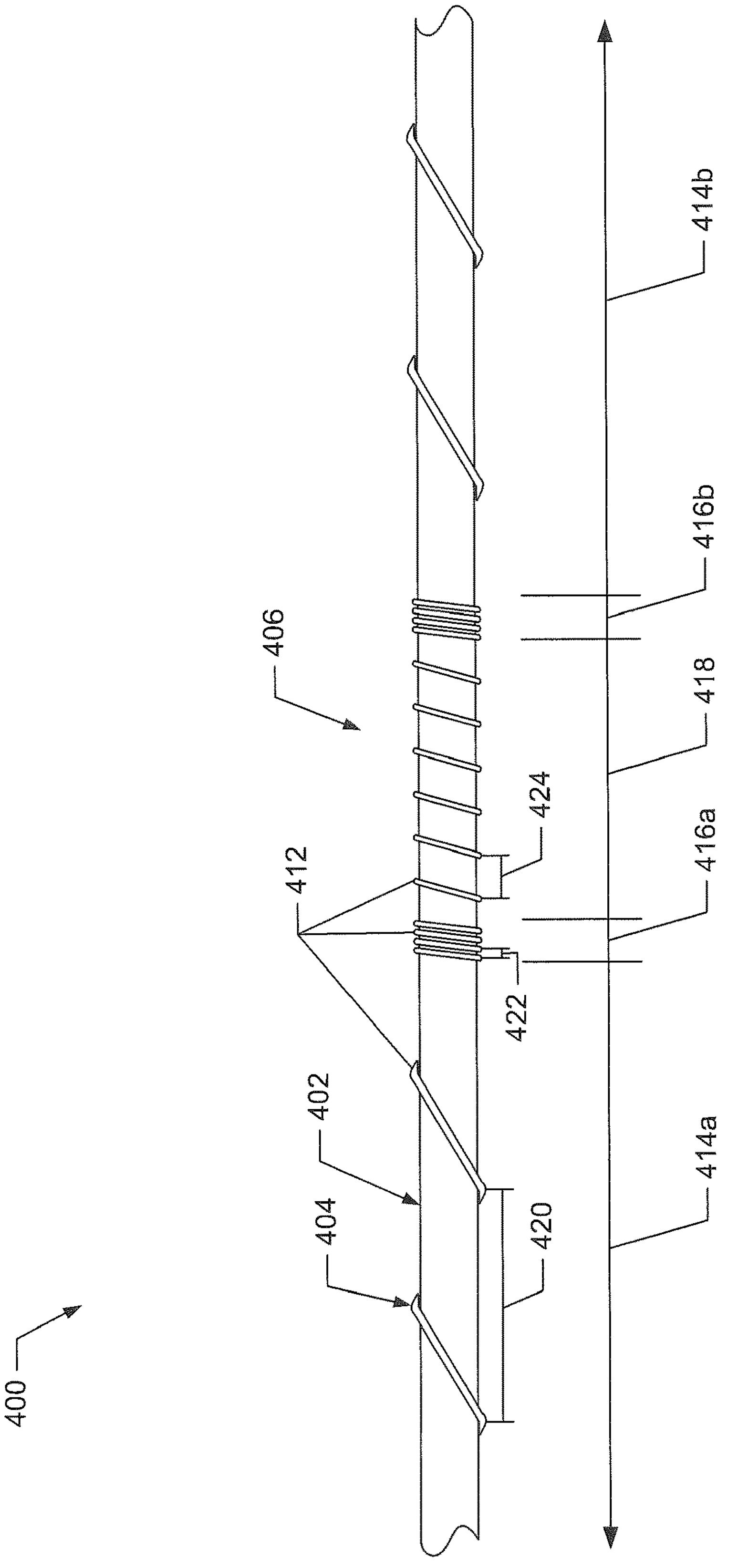
Figure 15:
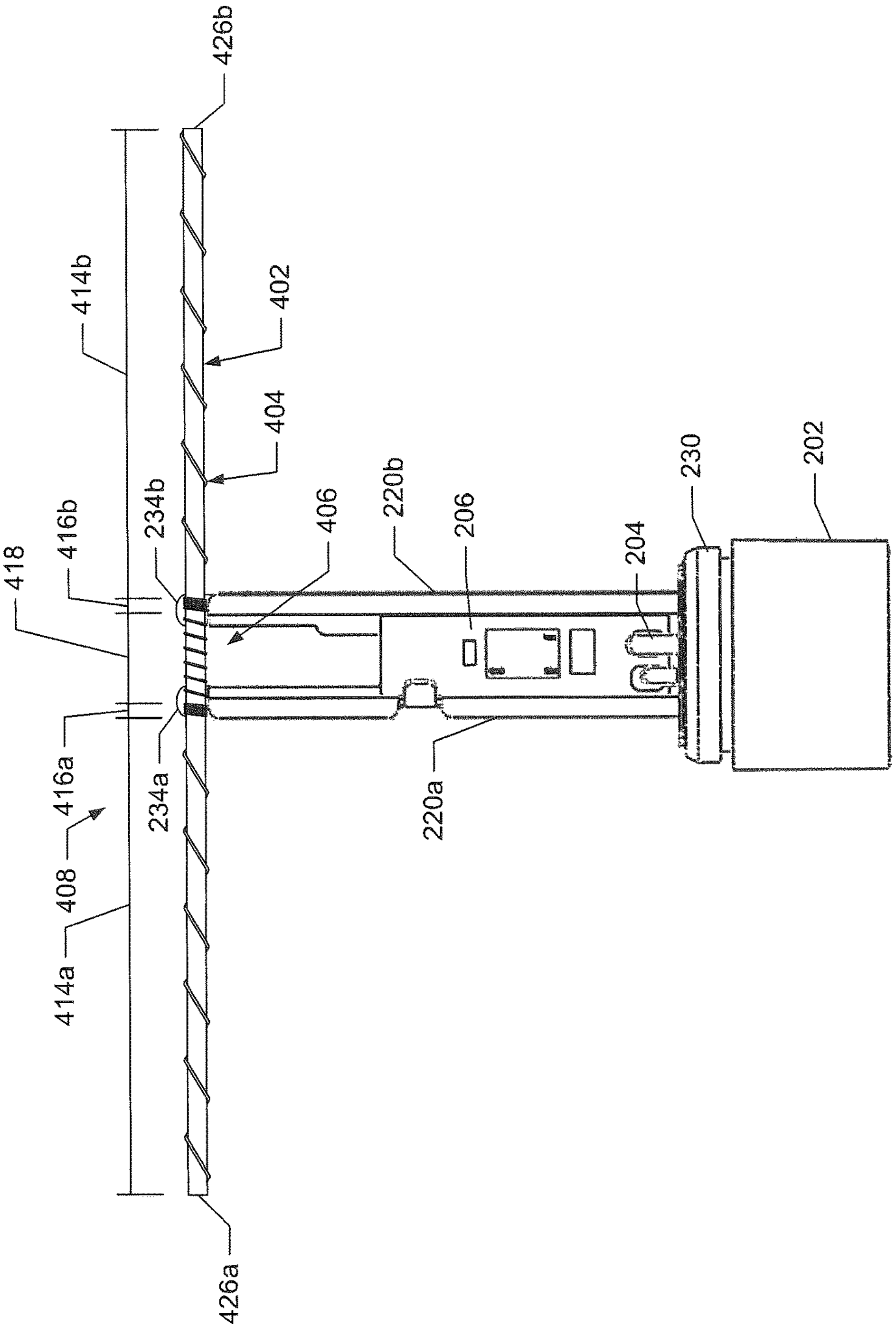
Figure 16:
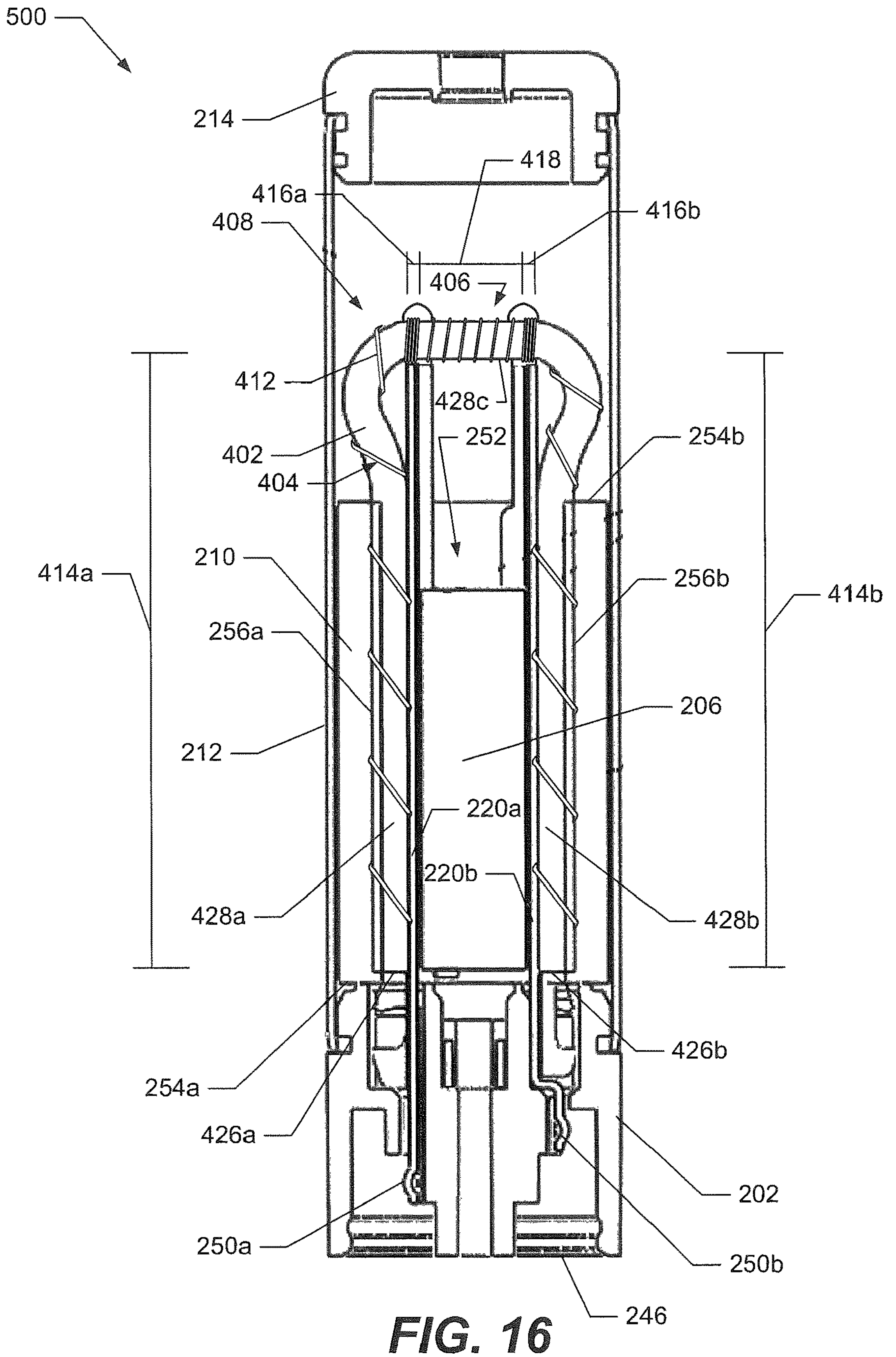
Figure 17:
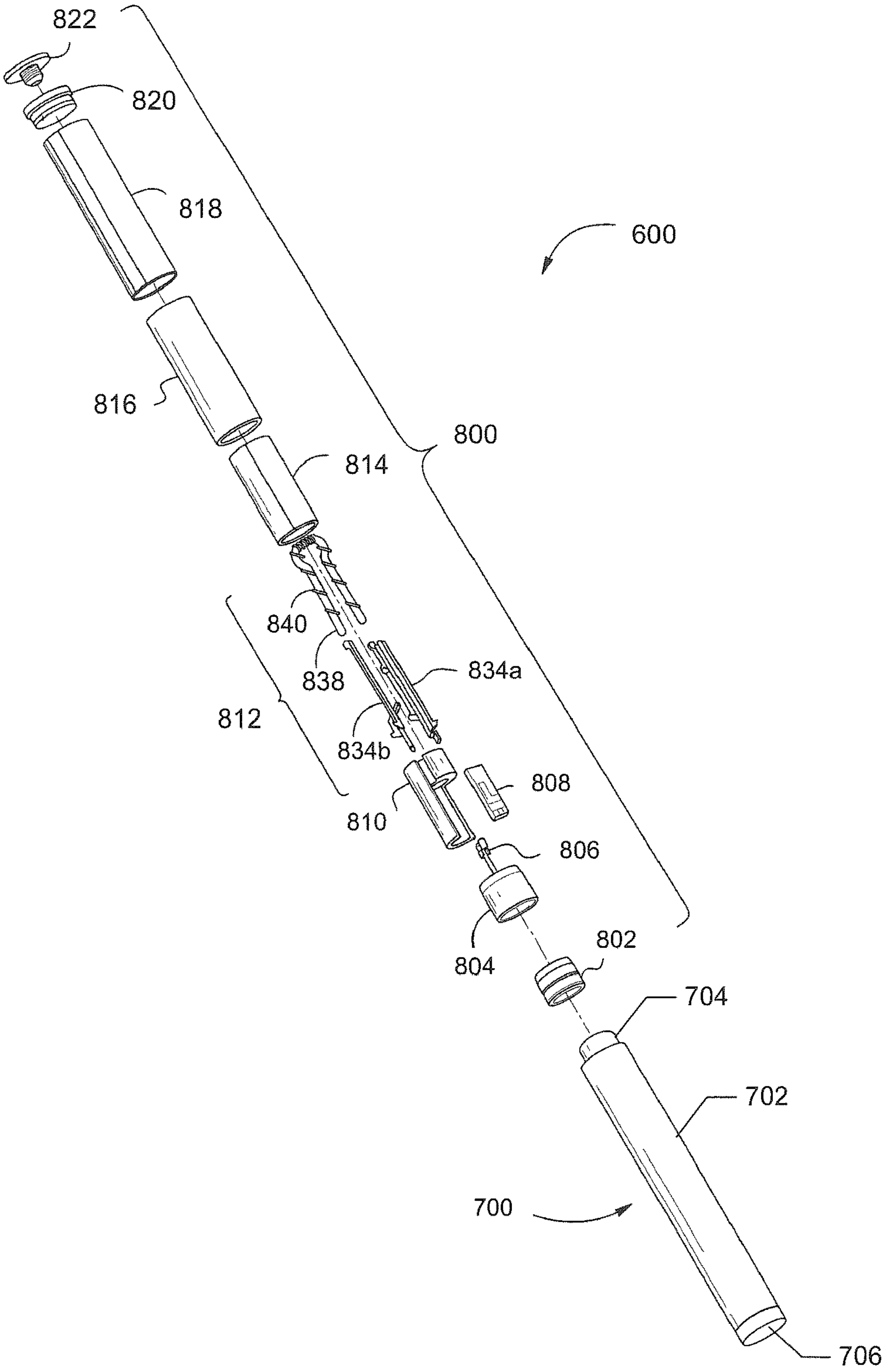
Figure 18:
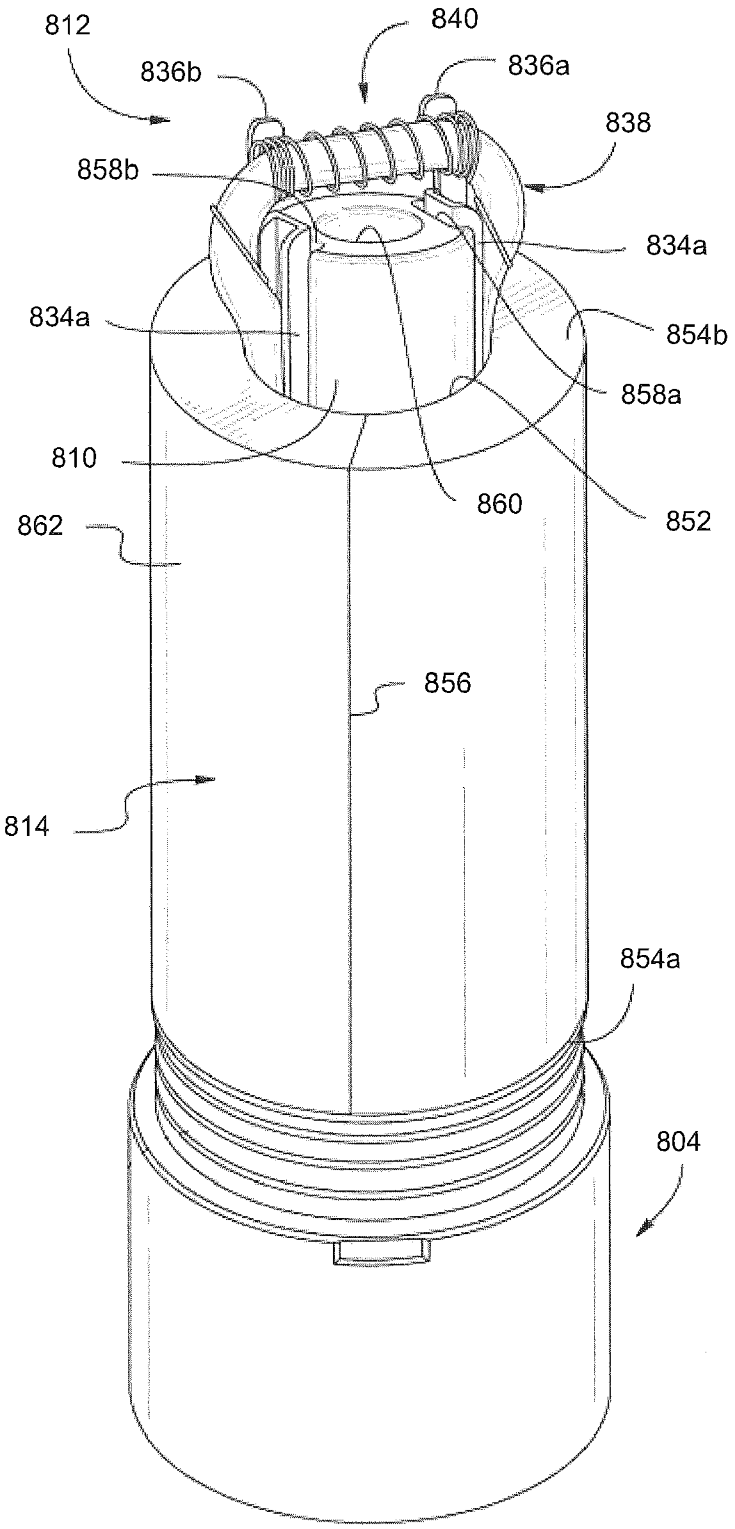
Figure 19:
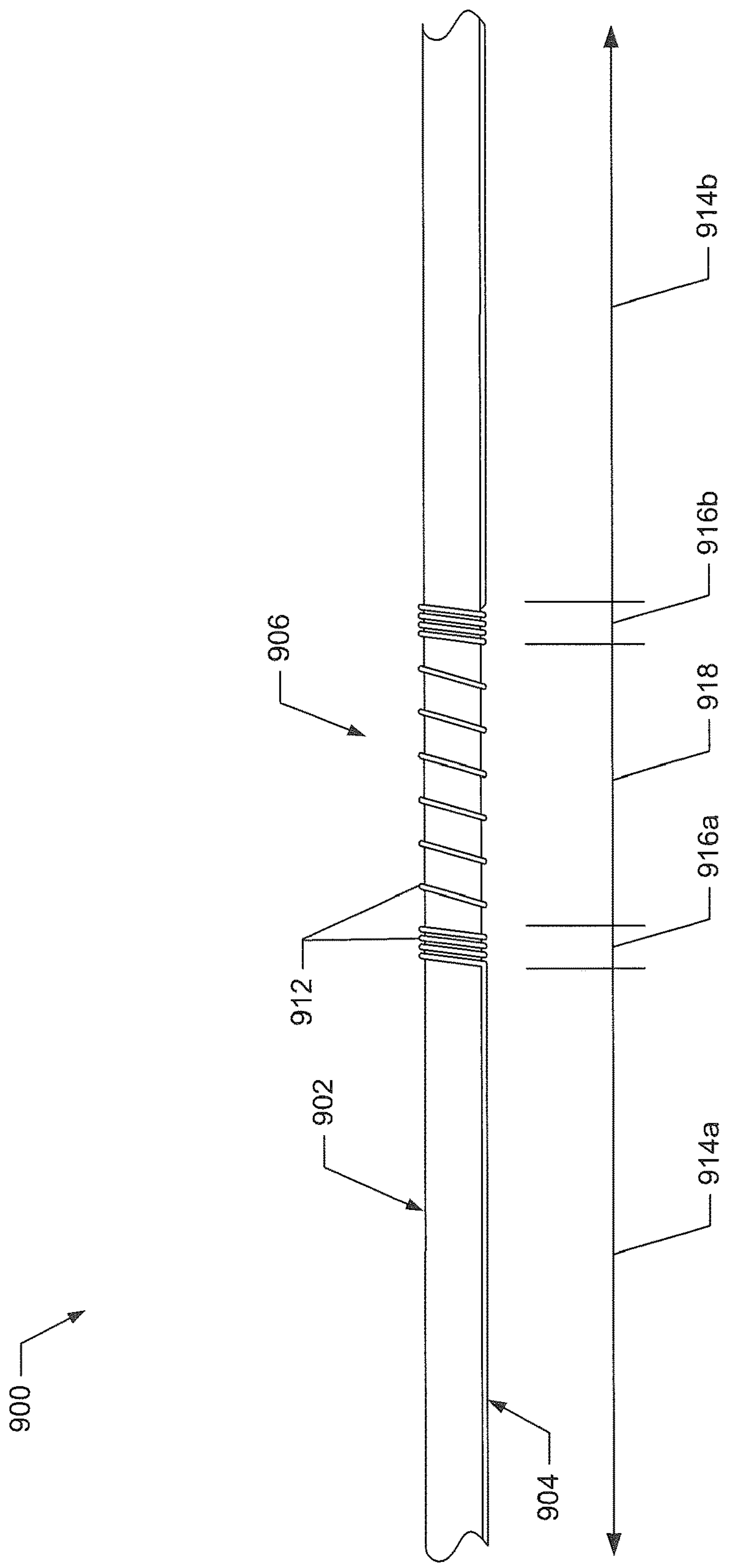
Figure 20:
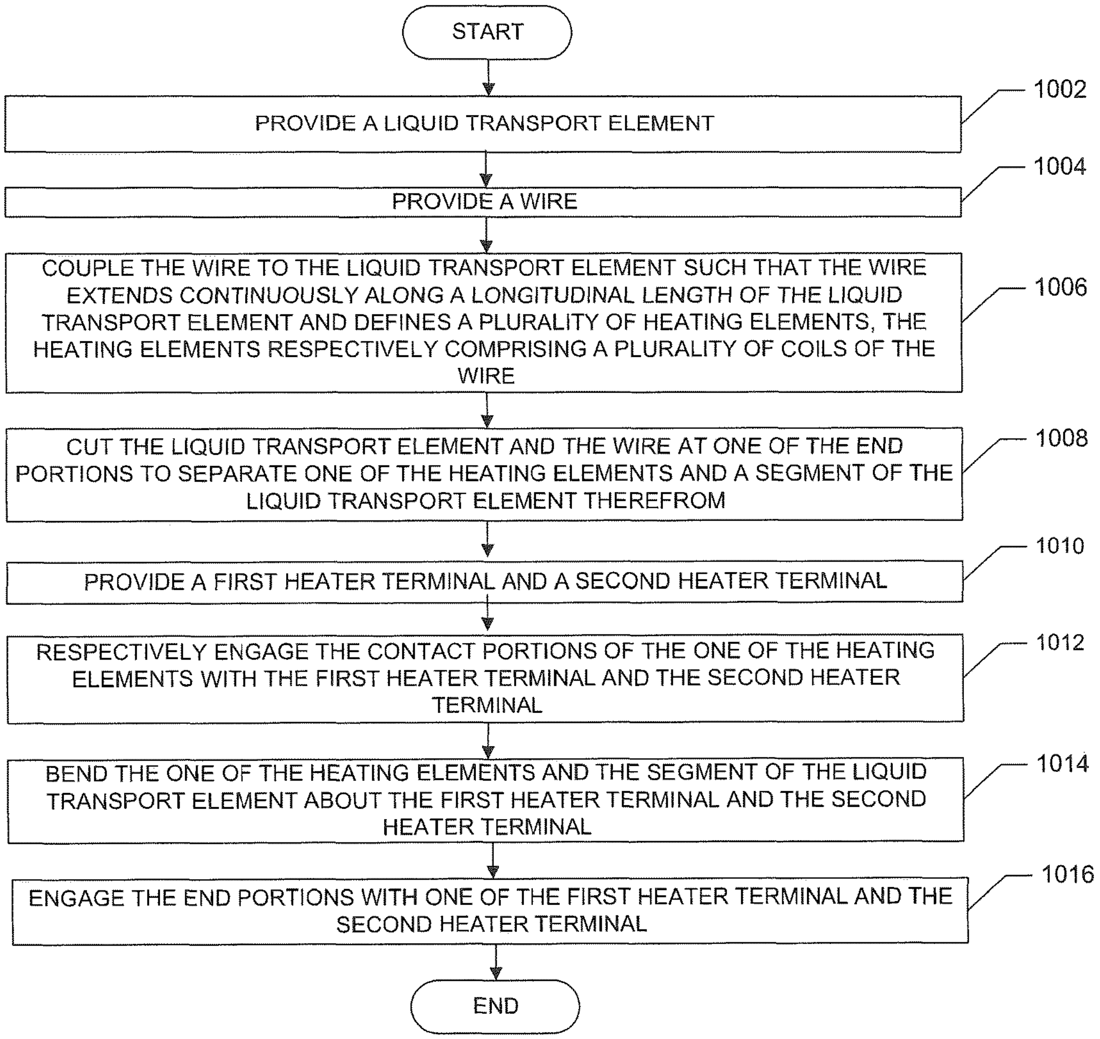

Having thus described the disclosure in the foregoing general terms, reference will now be made to the accompanying drawings, which are not necessarily drawn to scale, and wherein:

FIG. 1 illustrates a sectional view through a smoking article comprising a control body and a cartridge including an atomizer according to an example embodiment of the present disclosure;

FIG. 2 illustrates an exploded view of a cartridge for a smoking article comprising a base, a control component terminal, an electronic control component, an atomizer including a liquid transport element, a wire, and heater terminals, a reservoir substrate, an external shell, and a mouthpiece according to an example embodiment of the present disclosure;

FIG. 3 illustrates an enlarged exploded view of the base and the control component terminal of the cartridge of FIG. 2;

FIG. 4 illustrates an enlarged perspective view of the base and the control component terminal of FIG. 2 in an assembled configuration;

FIG. 5 illustrates an enlarged perspective view of the base, the control component terminal, the electronic control component, and the heater terminals of FIG. 2 in an assembled configuration;

FIG. 6 illustrates an enlarged perspective view of the base, the control component terminal, the electronic control component, and atomizer of FIG. 2 in an assembled configuration;

FIG. 7 illustrates an enlarged bottom perspective view of the base, the control component terminal, the electronic control component, and the atomizer of FIG. 2 in an assembled configuration;

FIG. 8 illustrates a perspective view of the base, the atomizer, and the reservoir substrate of FIG. 2 in an assembled configuration;

FIG. 9 illustrates a perspective view of the base and the external shell of FIG. 2 in an assembled configuration;

FIG. 10 illustrates a perspective view of the cartridge of FIG. 2 in an assembled configuration;

FIG. 11 illustrates a first partial perspective view of the cartridge of FIG. 2 and a receptacle for a control body according to an example embodiment of the present disclosure;

FIG. 12 illustrates an opposing second partial perspective view of the cartridge of FIG. 2 and the receptacle of FIG. 11;

FIG. 13 illustrates a partial side view of an input for production of a plurality of atomizers comprising a liquid transport element and a wire continuously wound about the liquid transport element according to an example embodiment of the present disclosure;

FIG. 14 illustrates an enlarged view of section A from FIG. 13;

FIG. 15 illustrates the base, electronic control component, control component terminal and heater terminals of FIG. 2 partially assembled with a segment of the input of FIG. 13 to form an atomizer;

FIG. 16 illustrates a modified cross-sectional view through a cartridge comprising the atomizer of FIG. 15;

FIG. 17 illustrates a partially exploded view of an aerosol delivery device including a control body in a assembled configuration and a cartridge in an exploded configuration, the cartridge comprising a base shipping plug, a base, a control component terminal, an electronic control component, a flow tube, an atomizer, a reservoir substrate, an external shell, a label, a mouthpiece, and a mouthpiece shipping plug according to an example embodiment of the present disclosure;

FIG. 18 illustrates an enlarged perspective view of the base, the atomizer, the flow tube, and the reservoir substrate of FIG. 17 in an assembled configuration;

FIG. 19 illustrates an enlarged partial view of an input for production of a plurality of atomizers comprising a liquid transport element and a wire according to an alternate embodiment of the present disclosure in which the wire is not continuously wound about the liquid transport element; and FIG. 20 illustrates a schematic view of a method of forming a plurality of atomizers according to an example embodiment of the present disclosure.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure provides descriptions of aerosol delivery devices that use electrical energy to heat a material (preferably without combusting the material to any significant degree) to form an inhalable substance; such articles most preferably being sufficiently compact to be considered "hand-held" devices. In certain highly preferred embodiments, the aerosol delivery devices can be characterized as smoking articles. As used herein, the term "smoking article" is intended to mean an article or device that provides some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. As used herein, the term "smoking article" does not necessarily mean that, in operation, the article or device produces smoke in the sense of the aerosol resulting from by-products of combustion or pyrolysis of tobacco, but rather, that the article or device yields vapors (including, e.g., vapors within aerosols that can be considered to be visible aerosols that might be considered to be described as smoke-like) resulting from volatilization or vaporization of certain components of the article or device. In highly preferred embodiments, articles or devices characterized as smoking articles incorporate tobacco and/or components derived from tobacco.

Articles or devices of the present disclosure also can be characterized as being vapor-producing articles, aerosol delivery articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, smoking articles of the present disclosure may be subjected to many of the physical actions employed by an individual in using a traditional type of smoking article (e.g., a cigarette, cigar or pipe that is employed by lighting and inhaling tobacco). For example, the user of a smoking article of the present disclosure can hold that article much like a traditional type of smoking article, draw on one end of that article for inhalation of aerosol produced by that article, take puffs at selected intervals of time, etc.

Smoking articles of the present disclosure generally include a number of components provided within an outer shell or body. The overall design of the outer shell or body can vary, and the format or configuration of the outer body defining the overall size and shape of the smoking article can vary. Typically, an elongated body resembling the shape of a cigarette or cigar can be a formed from a single, unitary shell; or the elongated body can be formed of two or more separable pieces. For example, a smoking article can comprise an elongated shell or body that can be substantially tubular in shape and, as such, resemble the shape of a conventional cigarette or cigar. In one embodiment, all of the components of the smoking article can be contained within one outer body or shell. Alternatively, a smoking article can comprise two or more shells that are joined and are separable. For example, a smoking article can possess at one end a control body comprising a shell containing one or more reusable components (e.g., a rechargeable battery and various electronics for controlling the operation of that article), and at the other end and removably attached thereto a shell containing a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various smoking article designs and component arrangements can be appreciated upon consideration of the commercially available electronic smoking articles, such as those representative products listed in the background art section of the present disclosure.

Smoking articles of the present disclosure most preferably comprise some combination of a power source (i.e., an electrical power source), at least one control component (e.g., means for actuating, controlling, regulating and ceasing power for heat generation, such as by controlling electrical current flow from the power source to other components of the article), a heater or heat generation component (e.g., an electrical resistance heating element or component commonly referred to as an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the smoking article for aerosol inhalation (e.g., a defined air flow path through the article such that aerosol generated can be withdrawn therefrom upon draw).

Alignment of the components within the article can vary. In specific embodiments, the aerosol precursor composition can be located near an end of the article (e.g., within a cartridge, which in certain circumstances can be replaceable and disposable), which may be proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof. Additionally, the selection of various smoking article components can be appreciated upon consideration of the commercially available electronic smoking articles, such as those representative products listed in the background art section of the present disclosure.

A smoking article incorporates a battery or other electrical power source to provide current flow sufficient to provide various functionalities to the article, such as resistive heating, powering of control systems, powering of indicators, and the like. The power source can take on various embodiments. Preferably, the power source is able to deliver sufficient power to rapidly heat the heating member to provide for aerosol formation and power the article through use for the desired duration of time. The power source preferably is sized to fit conveniently within the article so that the article can be easily handled; and additionally, a preferred power source is of a sufficiently light weight to not detract from a desirable smoking experience.

One example embodiment of a smoking article 100 is provided in FIG. 1. As seen in the cross-section illustrated therein, the smoking article 100 can comprise a control body 102 and a cartridge 104 that can be permanently or detachably aligned in a functioning relationship. Although a threaded engagement is illustrated in FIG. 1, it is understood that further means of engagement are encompassed, such as a press-fit engagement, interference fit, a magnetic engagement, or the like.

In specific embodiments, one or both of the control body 102 and the cartridge 104 may be referred to as being disposable or as being reusable. For example, the control body may have a replaceable battery or may be rechargeable and thus may be combined with any type of recharging technology, including connection to a typical electrical outlet, connection to a car charger (i.e., cigarette lighter receptacle), and connection to a computer, such as through a USB cable.

In the exemplified embodiment, the control body 102 includes a control component 106, a flow sensor 108, and a battery 110, which can be variably aligned, and can include a plurality of indicators 112 at a distal end 114 of an external shell 116. The indicators 112 can be provided in varying numbers and can take on different shapes and can even be an opening in the body (such as for release of sound when such indicators are present).

An air intake 118 may be positioned in the external shell 116 of the control body 102. A receptacle 120 also is included at a proximal attachment end 122 of the control body 102 and extends into a control body projection 124 to allow for ease of electrical connection with a an atomizer or a component thereof, such as a resistive heating element (described below) when the cartridge 104 is attached to the control body.

The cartridge 104 includes an external shell 126 with a mouth opening 128 at a mouthend 130 thereof to allow passage of air and entrained vapor (i.e., the components of the aerosol precursor composition in an inhalable form) from the cartridge to a consumer during draw on the smoking article 100. The smoking article 100 may be substantially rod-like or substantially tubular shaped or substantially cylindrically shaped in some embodiments.

The cartridge 104 further includes an atomizer 132 comprising a resistive heating element 134 comprising a wire coil in the illustrated embodiment and a liquid transport element 136 comprising a wick in the illustrated embodiment that is configured to transport a liquid. Various embodiments of materials configured to produce heat when electrical current is applied therethrough may be employed to form the wire coil. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), and ceramic (e.g., a positive temperature coefficient ceramic). The liquid transport element may also be formed from a variety of materials configured to transport a liquid. For example, the liquid transport element may comprise cotton and/or fiberglass in some embodiments. Electrically conductive heater terminals 138 (e.g., positive and negative terminals) at the opposing ends of the heating element 134 are configured to direct current flow through the heating element and configured for attachment to the appropriate wiring or circuit (not illustrated) to form an electrical connection of the heating element with the battery 110 when the cartridge 104 is connected to the control body 102. Specifically, a plug 140 may be positioned at a distal attachment end 142 of the cartridge 104. When the cartridge 104 is connected to the control body 102, the plug 140 engages the receptacle 120 to form an electrical connection such that current controllably flows from the battery 110, through the receptacle and plug, and to the heating element 134. The external shell 126 of the cartridge 104 can continue across the distal attachment end 142 such that this end of the cartridge is substantially closed with the plug 140 protruding therefrom.

A reservoir may utilize the liquid transport element 136 to transport an aerosol precursor composition to an aerosolization zone. One such example is shown in FIG. 1. As seen therein, the cartridge 104 includes a reservoir layer 144 comprising layers of nonwoven fibers formed into the shape of a tube encircling the interior of the external shell 126 of the cartridge, in this embodiment. An aerosol precursor composition is retained in the reservoir layer 144. Liquid components, for example, can be sorptively retained by the reservoir layer 144. The reservoir layer 144 is in fluid connection with the liquid transport element 136 (the wick in this embodiment). The liquid transport element 136 transports the aerosol precursor composition stored in the reservoir layer 144 via capillary action to an aerosolization zone 146 of the cartridge 104. As illustrated, the liquid transport element 136 may be in direct contact with the heating element 134 that is in the form of a metal wire coil in this embodiment.

In use, when a user draws on the article 100, the heating element 134 is activated (e.g., such as via a puff sensor), and the components for the aerosol precursor composition are vaporized in the aerosolization zone 146. Drawing upon the mouthend 130 of the article 100 causes ambient air to enter the air intake 118 and pass through the central opening in the receptacle 120 and the central opening in the plug 140. In the cartridge 104, the drawn air passes through an air passage 148 in an air passage tube 150 and combines with the formed vapor in the aerosolization zone 146 to form an aerosol. The aerosol may be whisked away from the aerosolization zone 146, pass through an air passage 152 in an air passage tube 154, and out the mouth opening 128 in the mouthend 130 of the article 100.

It is understood that a smoking article that can be manufactured according to the present disclosure can encompass a variety of combinations of components useful in forming an electronic smoking article. Reference is made for example to the smoking articles disclosed in U.S. patent application Ser. No. 13/536,438, filed Jun. 28, 2012, U.S. patent application Ser. No. 13/432,406, filed Mar. 28, 2012, U.S. patent application Ser. No. 13/602,871, filed Sep. 4, 2012, the disclosures of which are incorporated herein by reference in their entirety. Further to the above, representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, a single-use cartridge for use with an electronic smoking article is disclosed in U.S. patent application Ser. No. 13/603,612, filed Sep. 5, 2012, which is incorporated herein by reference in its entirety.

The various components of a smoking article according to the present disclosure can be chosen from components described in the art and commercially available. Examples of batteries that can be used according to the disclosure are described in U.S. Pat. App. Pub. No. 2010/0028766, the disclosure of which is incorporated herein by reference in its entirety.

An exemplary mechanism that can provide puff-actuation capability includes a Model 163PC01D36 silicon sensor, manufactured by the MicroSwitch division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Further description of current regulating circuits and other control components, including microcontrollers that can be useful in the present smoking article, are provided in U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., and U.S. Pat. No. 7,040,314 to Nguyen et al., all of which are incorporated herein by reference in their entireties.

The aerosol precursor, which may also be referred to as an aerosol precursor composition or a vapor precursor composition, can comprise one or more different components. For example, the aerosol precursor can include a polyhydric alcohol (e.g., glycerin, propylene glycol, or a mixture thereof). Representative types of further aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference.

Still further components can be utilized in the smoking article of the present disclosure. For example, U.S. Pat. No. 5,261,424 to Sprinkel, Jr. discloses piezoelectric sensors that can be associated with the mouth-end of a device to detect user lip activity associated with taking a draw and then trigger heating; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. App. Pub. No. 2009/0320863 by Fernando et al. discloses computer interfacing means for smoking devices to facilitate charging and allow computer control of the device; U.S. Pat. App. Pub. No. 2010/0163063 by Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. No. 8,156,944 to Hon; U.S. Pat. App. Pub. Nos. 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/

0024834 to Oglesby et al.; U.S. Pat. App. Pub. No. 2010/0307518 to Wang; and WO 2010/091593 to Hon. A variety of the materials disclosed by the foregoing documents may be incorporated into the present devices in various embodiments, and all of the foregoing disclosures are incorporated herein by reference in their entireties.

FIG. 2 illustrates an exploded view of an additional example embodiment of a cartridge 200 for a smoking article. The cartridge 200 may comprise a base 202, a control component terminal 204, an electronic control component 206, an atomizer 208, a reservoir substrate 210, an external shell 212, and a mouthpiece 214. As described in greater detail below, the atomizer 208 may comprise a liquid transport element 216, a heating element 218, and a first heater terminal 220*a* and a second heater terminal 220*b* (collectively, "heater terminals 220"). Note that the various embodiments of components described above in the cited references and/or included in commercially available aerosol delivery devices may be employed in embodiments of the cartridges described herein.

The cartridge 200 may be configured to couple to a control body to form a smoking article. Note that some of the above-described components of the cartridge 200 are optional. In this regard, by way of example, the cartridge 200 may exclude the control component terminal 204 and the electronic control component 206 in some embodiments.

FIG. 3 illustrates an enlarged exploded view of the base 202 and the control component terminal 204. The control component terminal 204 may define a clip 222 configured to engage the electronic control component 206 and form an electrical connection therewith. Further, the control component terminal 204 may include one or more protrusions 224*a*, 224*b* configured to engage the base 202, for example via interference fit, such that the control component terminal 204 is retained in engagement therewith. An end 226 of the control component terminal 204 may be configured to engage a control body, so as to establish an electrical connection therewith.

As illustrated, the base 202 may define a receptacle 228 configured to receive the control component terminal 204 therein. In this regard, as illustrated in FIG. 4, the control component terminal 204 may couple to the base 202. For example, the control component terminal 204 may be retained in the receptacle 228 of the base 202 via interference fit, for example due to contact between the protrusions 224*a*, 224*b* and the base. As described below, the control component terminal 204 may extend through the base 202 to a position at which it may form an electrical connection with a control body to which the cartridge 200 connects. Further, the base 202 may define threads or protrusions 230 configured to engage the external shell 212, as will be described below.

As illustrated in FIG. 5, the control component terminal 204 may couple to the electronic control component 206 such that an electrical connection is established therebetween. Accordingly, when the cartridge 200 is coupled to a control body, the electronic control component 206 may communicate therewith through the control component terminal 204. The electronic control component 206 may be configured to perform one or more of a variety of functions. Further, the electronic control component 206 may be configured as purpose-specific analog and/or digital circuitry with or without a processor, or the electronic control component may comprise hardware, software, or a combination of hardware and software. Accordingly, any or all of the functions performed by or in conjunction with the electronic control component 206 may be embodied in a computer-readable storage medium having computer-readable program code portions stored therein that, in response to execution by a processor, cause an apparatus to at least perform or direct the recited functions. In one particular instance, upon establishment of communication between the electronic control component 206 and a control body, the electronic control component may be configured to provide an authentication code or other appropriate indicia to the control body. In such instances, the control body may be configured to evaluate the authentication indicia to determine whether the cartridge 200 is authorized for use with the control body. However, the electronic control component 206 may perform various other functions. Various examples of electronic control components and functions performed thereby are described in U.S. patent application Ser. No. 13/647,000, filed Oct. 8, 2012, which is incorporated herein by reference in its entirety.

Further, as illustrated in FIG. 2, in some embodiments the electronic control component 206 may comprise two portions 206*a*, 206*b*. A first portion 206*a* of the electronic control component 206 may include hardware and/or software configured to perform one or more functions (e.g., as described above), whereas the second portion 206*b* of the electronic control component may provide structural support thereto. Accordingly, the electronic control component 206 may be provided in two-piece form in some embodiments. This form may allow for substitution of the first portion 206*a*, as may be desirable to change the functionality of the electronic control component 206, while still employing the same second portion 206*b* for structural support.

As illustrated in FIG. 5, heater terminals 220 may define a plurality of walls, which may extend at least partially around the electronic control component 206 in some embodiments such that the electronic control component is received therebetween. This configuration may allow the heater terminals 220 to provide support to the electronic control component 206, for example by contact therewith, such that the electronic control component is securely retained in place. In the illustrated embodiment, each terminal 220 respectively defines a first wall 232*a*, and a second wall 232*b*, which may be substantially perpendicular to one another. Further, the heater terminals 220 may define first and second tabs 234*a*, 234*b* (collectively, "tabs 234"). The tabs 234 may be positioned at the end of the heater terminals 220 distal to the base 202. In some embodiments the heater terminals 220 may be stamped or otherwise formed from a sheet of a metal material. However, the heater terminals 220 may be formed in various other manners and formed from any of a variety of conductive materials.

FIG. 6 illustrates the completed atomizer 208 coupled to the base 202 via the heater terminals 220. As illustrated in FIG. 6, the tabs 234 may be substantially parallel to the second walls 232*b* of the terminals 220. This configuration may assist in retaining the liquid transport element 216 in place, because the liquid transport element may be received between opposing faces defined by the second walls 232*b* and the tabs 234.

In this regard, as further illustrated in FIG. 6, the liquid transport element 216 may be configured in a substantially U-shaped configuration. The liquid transport element 216, which may comprise a wick (e.g., a fiberglass wick) in some embodiments, may be either preformed in the U-shaped configuration or bent to define this configuration. A first distal arm 236*a* and a second distal arm 236*b* (collectively, "distal arms 236") of the liquid transport element 216 may respectively extend along the first and second heater terminals 220*a*, 220*b* and respectively terminate at a first liquid transport element end 238*a* and a second liquid transport element end 238*b* (collectively, "liquid transport element ends 238"). Further a center section 236*c* of the liquid transport element 216, at which the heating element 218 is positioned, may extend between the heater terminals 220.

The heating element 218 extends at least partially about the liquid transport element 216 at a position between the first liquid transport element end 238*a* and the second liquid transport element end 238*b*. In some embodiments, the heating element 218 may comprise a wire 240 defining a plurality of coils wound about the liquid transport element 216 and extending between a first wire end 242*a* and a second wire end 242*b* (collectively, "wire ends 242"), as illustrated in FIG. 6. The wire 240 may comprise a material configured to produce heat when electrical current is provided therethrough. For example, the wire 240 may comprise Kanthal (FeCrAl), Nichrome, Molybdenum disilicide ($MoSi_2$), molybdenum silicide (MoSi), Molybdenum disilicide doped with Aluminum ($Mo(Si,Al)_2$), or ceramic (e.g., a positive temperature coefficient ceramic) in some embodiments, although various other materials may be employed in other embodiments. In some embodiments the heating element 218 may be formed by winding the wire 240 about the liquid transport element 216 as described in U.S. patent application Ser. No. 13/708,381, filed Dec. 7, 2012, which is incorporated herein by reference in its entirety. However, various other embodiments of methods may be employed to form the heating element 218, and various other embodiments of heating elements may be employed in the atomizer 208.

The tabs 234 may be configured to contact the wire ends 242 such that an electrical connection is established therebetween. In this regard, the tabs 234 may be configured to be positioned adjacent to the heating element 218 such that the tabs directly contact one or more coils of the wire 240. Direct contact, as used herein, refers to physical contact between the wire 240 and the heater terminals 220. However, direct contact, as used herein, also encompasses embodiments in which one or more welds couple the wire 240 and the heater terminals 220. A weld, as used herein, refers to a solder, flux, braze, or other material that is deposited in liquid or molten form and hardens to form a connection.

In one embodiment, as illustrated in FIG. 6, the spacing of the coils (i.e. the distance therebetween) may be less proximate the wire ends 242 than proximate a center of the heating element 218. For example, in one embodiment the coils of the heating element 218 may touch one another at the wire ends 242, whereas the coils may be spaced apart such that there is not contact therebetween at locations between the wire ends. By decreasing the spacing between the coils of the wire 240 at the wire ends 242, more coils may contact the tabs 234, such that an improved electrical connection between the heating element 218 and the heater terminals 220 may be established.

As noted above, the electronic control component 206 may be received between the heater terminals 220 and the distal arms 236 of the liquid transport element 216. However, a gap 244 may be provided between the electronic control component 206 and the heating element 218. The gap 244 may reduce the amount of heat transferred to the electronic control component 206 from the heating element 218, for example by preventing direct conduction therebetween. Accordingly, the risk of damage to the electronic control component 206 from exposure to heat produced by the heating element 218 may be reduced. In some embodiments, a structure, which may be referred to as a chimney, may be employed to direct airflow through the cartridge to the heating element 218 in order to precisely regulate the flow of air therethrough.

FIG. 7 illustrates an alternative perspective view of the base 202, the control component terminal 204, the electronic control component 206, and the atomizer 208 after they are coupled to one another. In particular, FIG. 7 illustrates a view of a connector end 246 of the base 202. As illustrated, a central opening 248 may be defined in the base 202. The central opening 248 may be configured to receive airflow therethrough from a control body and direct the airflow toward the heating element 218 of the atomizer 208.

The heater terminals 220 may engage the base 202 and respectively extend to a first end 250*a* and a second end 250*b* (collectively, "ends 250"), which may be configured to engage a control body, so as to establish an electrical connection therewith. In this regard, as illustrated in FIG. 7, the end 226 of the control component terminal 204 and the ends 250 of the heater terminals 220 may be exposed at the connector end 246 of the base 202. The end 226 of the control component terminal 204 and the ends 250 of the heater terminals 220 may be located at differing positions within the base 202 such that they make connections with components at different locations within the control body, and avoid unintended contact therebetween.

In this regard, the end 226 of the control component terminal 204 and the ends 250 of the heater terminals 220 may be located at differing radial distances from the central opening 248. In the illustrated embodiment, the end 226 of the control component terminal 204 is located closest to the central opening 248, the second end 250*b* of the second heater terminal 220*b* is located farthest from the central opening, and the first end 250*a* of the second heater terminal 220*a* is located at a radial distance therebetween. Further, the end 226 of the control component terminal 204 and the ends 250 of the heater terminals 220 may extend to a plurality of different depths within the base 202. In the illustrated embodiment, the end 226 of the control component terminal 204 extends through the base 202 to a greatest depth, the second end 250*b* of the second heater terminal 220*b* extends through the base to the smallest depth, and the first end 250*a* of the first heater terminal 220*a* extends through the base to a depth therebetween.

FIG. 8 illustrates a perspective view of the assembly of FIGS. 6 and 7 after the reservoir substrate 210 is coupled thereto. The reservoir substrate 210 may be configured to hold an aerosol precursor composition. The aerosol precursor composition may comprise a variety of components including, by way of example, glycerin, nicotine, tobacco, tobacco extract, and/or flavorants. Various components that may be included in the aerosol precursor composition are described in U.S. Pat. No. 7,726,320 to Robinson et al., which is incorporated herein by reference.

The reservoir substrate 210 may define a cavity 252 extending therethrough from a first reservoir end 254*a* to a second reservoir end 254*b* (collectively, "reservoir ends 254"), wherein the first reservoir end is positioned proximate the base 202. In this regard, the reservoir substrate 210 may define a hollow tubular configuration. Note that although generally described herein as defining a hollow tubular configuration, the reservoir substrate 210 may define other shapes and configurations in other embodiments. The aerosol precursor composition may be retained within the material defining the reservoir substrate 210 itself, as opposed to within the cavity 252. This configuration may allow for airflow through the base 202, into and through the cavity 252, and past the heating element 218.

The reservoir substrate 210 can comprise one or more of various materials and can be formed in a variety of different manners. In one embodiment the reservoir substrate 210 can be formed from a plurality of combined layers that can be concentric or overlapping. For example, the reservoir substrate 210 can be a continuous sheet of a material that is rolled to form the hollow tubular configuration. In other embodiments, the reservoir substrate 210 can be substantially a unitary component. For example, the reservoir substrate 210 can be shaped or molded so as to be a singular preformed element in the form of a substantially hollow tube, which may be substantially continuous in composition across the length and thickness thereof.

The reservoir substrate 210 can be formed from a material that is rigid or semi-rigid in some embodiments, while retaining the ability to store a liquid product such as, for example, an aerosol precursor composition. In certain embodiments, the material of the reservoir substrate 210 can be absorbent, adsorbent, or otherwise porous so as to provide the ability to retain the aerosol precursor composition. As such, the aerosol precursor composition can be characterized as being coated on, adsorbed by, or absorbed in the material of the reservoir substrate 210. The reservoir substrate 210 can be positioned within the cartridge 200 such that the reservoir substrate is in contact with the liquid transport element 216. More particularly, the reservoir substrate 210 can be manufactured from any material suitable for retaining the aerosol precursor composition (e.g., through absorption, adsorption, or the like) and allowing wicking away of the precursor composition for transport to the heating element 218.

The material of the reservoir substrate 210 may be suitable for forming and maintaining an appropriate shape. The material of the reservoir substrate 210 can be heat resistant so as to retain its structural integrity and avoid degradation at least at a temperature proximal to the heating temperature provided by the heating element 218. However, the reservoir substrate 210 need not be heat resistant to the full temperature produced by the heating element 218 due to the reservoir substrate being out of contact therewith. The size and strength of the reservoir substrate 210 may vary according to the features and requirements of the cartridge 200. In particular embodiments, the reservoir substrate 210 can be manufactured from a material suitable for a high-speed, automated manufacturing process. Such processes may reduce manufacturing costs compared to traditional woven or non-woven fiber mats. According to one embodiment, the reservoir can be manufactured from a cellulose acetate tow which can be processed to form a hollow acetate tube.

In certain embodiments, the reservoir substrate 210 can be provided in a form such that at least part of the cavity 252 is shaped and dimensioned to accommodate one or more other components of the cartridge 200. In some embodiments, the term "shaped and dimensioned" can indicate that a wall of the reservoir substrate 210 at the cavity 252 includes one or more indentations or protrusions that cause the interior of the reservoir substrate to have a shape that is other than substantially smooth and continuous. In other embodiments, the hollow nature of the reservoir substrate 210 can be sufficient to allow for accommodation of further components of the cartridge 200 without the need for formation of cavities or protrusions. Thus, the cartridge 200 can be particularly beneficial in that the reservoir substrate 210 can be pre-formed and can have a hollow interior defining the cavity 252 with a wall that is shaped and dimensioned to accommodate a further component of the cartridge in a mating arrangement. This particularly can facilitate ease of assembly of the cartridge 200 and can maximize the volume of the reservoir substrate 210 while also providing sufficient space for aerosol formation.

In the illustrated embodiment, the cavity 252 extending through the reservoir substrate 210 is shaped and dimensioned to accommodate at least a portion of the atomizer 208. Specifically, the reservoir substrate 210 includes two diametrically opposed grooves **256*a*, 256*b* (collectively, "grooves 256") at the cavity 252. As illustrated, the grooves 256 may extend substantially the entire length of the reservoir substrate 210 from the first end 254*a* to the second end 254*b* thereof. In light of the reservoir substrate 210 defining the cavity 252 therethrough, the atomizer 208 can be easily positioned interior to the reservoir substrate during assembly of the smoking article. Likewise, since the cavity 252 is shaped and dimensioned to mate with the atomizer 208, the combination can be easily assembled, and the atomizer can snugly mate with the reservoir substrate 210 while simultaneously placing the liquid transport element 216** in fluid connection with the reservoir substrate.

In this regard, the grooves 256 may be configured to receive the liquid transport element 216 at least partially therein. More particularly, the distal arms 236 of the liquid transport element 216 may be received in the grooves 256. Thus, the liquid transport element 216 may extend substantially entirely through the reservoir substrate 210 such that the liquid transport element ends 238 are positioned proximate the first reservoir end **254*a*. Further, the heater terminals 220 may extend through the cavity 252 through the reservoir substrate 210. In some embodiments the heater terminals 220 may be partially or fully received in the grooves 256. Additionally, the electronic control component 206 may be at least partially received in the cavity 252 through the reservoir substrate 210**.

By adapting the cavity 252 of the reservoir substrate 210 to accommodate the atomizer 208, and/or various other components of the cartridge 200, available open space in the cartridge can be fully maximized by extending the reservoir substrate into the previously open spaces. As a result, the overall size and capacity of the reservoir substrate 210 can be increased in comparison to traditional woven or non-woven fiber mats that are typically utilized in electronic smoking articles. The increased capacity allows the reservoir substrate 210 to hold an increased amount of the aerosol precursor composition which may, in turn, result in longer use and enjoyment of the cartridge 200 by the end user.

As illustrated in FIG. 8, the atomizer 208 may extend through the cavity 252 of the reservoir substrate 210 such that the heating element 218 is positioned proximate the second reservoir end **254*b*. More particularly, the atomizer 208 may extend through the cavity 252 such that the heating element 218 is positioned past the second reservoir end 254*b* and is positioned outside of the cavity. This embodiment may reduce the heat directly applied by the heating element 218 to the reservoir substrate 210 such that the amount of the aerosol precursor composition vaporized by the heating element is controlled in part by the flow of the aerosol precursor composition through the liquid transport element 216** to the heating element. Accordingly, the amount of aerosol precursor composition vaporized may be more precisely controlled. However, in other embodiments, it is not necessary for the atomizer to extend beyond the second reservoir end, and the atomizer can be positioned relative to the reservoir substrate such that the heating element is received within the cavity of the reservoir substrate.

The reservoir substrate 210 includes an exterior surface 258 that can be substantially shaped and adapted to conform to an interior surface 260 of the external shell 212. In this regard, the external shell 212 may define a tubular shape with a cavity 262 therethrough sized to receive the reservoir substrate 210. For example, an inner radius of the external shell 212 may substantially correspond to, or may be slightly larger than, an outer radius of the reservoir substrate 210. Accordingly, the external shell 212 may be received over the reservoir substrate 210 and coupled to the base 202, as illustrated in FIG. 9. In this regard, one or more indentations 264 may engage the threads or protrusions 230 on the base 202 such that coupling is retained therebetween.

As illustrated in FIG. 10, the external shell 212 may couple to the mouthpiece 214 such that the cavity 262 defined by the external shell is at least partially enclosed. More particularly, in one embodiment one or more indentations 266 may engage threads or protrusions 268 on the mouthpiece 214 (see, e.g., FIG. 2) such that coupling therebetween is retained. The mouthpiece 214 defines one or more openings 270 through which air mixed with aerosol produced by the atomizer 208 may be directed when a user draws on the mouthpiece, as described in accordance with the above-noted example embodiments of smoking articles.

FIGS. 11 and 12 illustrate a receptacle 300 that may be included in a control body configured to engage the cartridge 200 and the various other embodiments of cartridges described below. As illustrated, the receptacle 300 may comprise protrusions or threads 302 that are configured to engage an external shell of the control body such that a mechanical connection is formed therebetween. The receptacle 300 may define an outer surface 304 configured to mate with an inner surface 272 of the base 202. In one embodiment the inner surface 272 of the base 202 may define a radius that is substantially equal to, or slightly greater than, a radius of the outer surface 304 of the receptacle 300. Further, the receptacle 300 may define one or more protrusions 306 at the outer surface 304 configured to engage one or more recesses 274 defined at the inner surface 272 of the base 202. However, various other embodiments of structures, shapes, and components may be employed to couple the base 202 to the receptacle 300. In some embodiments the connection between the base 202 and the receptacle 300 of the control body may be substantially permanent, whereas in other embodiments the connection therebetween may be releasable such that, for example, the control body may be reused with one or more additional cartridges.

The receptacle 300 may further comprise a plurality of electrical contacts 308*a-c* respectively configured to contact the end 226 of the control component terminal 204 and the ends 250 of the heater terminals 220. The electrical contacts 308*a-c* may be positioned at differing radial distances from a central opening 310 through the receptacle 300 and positioned at differing depths within the receptacle 300. The depth and radius of each of the electrical contacts 308*a-c* is configured such that the end 226 of the control component terminal 204 and the ends 250 of the heater terminals 220 respectively come into contact therewith when the base 202 and the receptacle 300 are joined together to establish an electrical connection therebetween.

In the illustrated embodiment the electrical contacts 308*a-c* comprise circular metal bands of varying radii positioned at differing depths within the receptacle 300. When the electrical contacts 308*a-c* comprise circular bands and the end 226 of the control component terminal 204 and the ends 250 of the heater terminals 220 extend to corresponding depths and radii within the base 202, electrical connections between the base and the receptacle 300 may be established regardless of the rotational orientation of the base with respect to the receptacle. Accordingly, connection between the base 202 of the cartridge 200 and the receptacle 300 of the control body may be facilitated. The electrical contacts 308*a-c* may be respectively coupled to a plurality of control body terminals 312*a-c* that connect to a plurality of components within the control body such as a battery and a controller therefor.

Further, when the base 202 of the cartridge 200 and the receptacle 300 of the control body are coupled together, a fluid connection may also be established. In this regard, the receptacle 300 may define a fluid pathway configured to receive air from an ambient environment and direct the air to the cartridge 200 when a user draws thereon. More particularly, in one embodiment the receptacle 300 may define a rim 314 with a radially extending notch 316 defined therein. Further a longitudinally extending recessed slot 318 may extend from the notch 316 to an opening 320. The opening 320 may define a cutout or a hole through a portion of the receptacle in some embodiments. Thus, when the receptacle 300 is engaged with the end of an external shell or body of a corresponding control body, the fluid pathway through the notch 316, the slot 318, and the opening 320 may remain open. Air drawn through this path may then be directed through the central opening 310 of the receptacle 300 and the central opening 248 of the base 202 when the receptacle and the base are connected to one another. Thus, air may be directed from the control body through the cartridge 200 in the manner described above when a user draws on the mouthpiece 214 of the cartridge.

Accordingly, the above-described cartridge 200 may provide benefits in terms of ease of assembly and ease of attachment to the receptacle 300 of a control body. In particular, with respect to the cartridge 200, assembly thereof may be simplified in that the components thereof may be generally axially assembled. More specifically, in one embodiment the control component terminal 204 may be coupled to the base 202, the electronic control component 206 may be coupled to the control component terminal, the heater terminals 220 may be coupled to the base, the heating element 218 may be coupled to the liquid transport element 216 and the combination thereof may be coupled to the heater terminals to form the atomizer, the reservoir substrate 210 may be coupled to the atomizer, the external shell 212 may be coupled to the base, and the mouthpiece 214 may be coupled to the external shell.

As described above, embodiments of smoking articles may employ an atomizer comprising a heating element formed from a wire coil. In the example embodiment illustrated in FIG. 6, the heating element 218 is wound about a center section 236*c* of the liquid transport element 216. The heating element 218 does not extend to the distal arms 236*a*, 236*b* of the liquid transport element 216. In this regard, production of atomizers comprising a heating element that is formed on only a portion of the length of a liquid transport element may present certain challenges that may make economical production thereof difficult. In this regard, production of heating elements that only extend along a portion of the length of the liquid transport element may require usage of a "start and stop" winding process, wherein a wire is brought into contact with and wound about the liquid transport element, extends along a section, and then stops at the desired end of the heating element, at which the wire is removed from contact with the liquid transport element. This process may then be repeated at additional spaced locations along the longitudinal length of the liquid transport element, or the process may be conducted once for an individual liquid transport element segment sized for use in the atomizer. Regardless of the particular details of the process employed, discrete production of individual heating elements may involve repeatedly starting and stopping the supply of wire to the liquid transport element and winding the wire thereon. Thus, the production of heating elements may be relatively expensive and/or slow due to the repeated starting and stopping involved during the production process.

Accordingly, the present disclosure provides embodiments of methods of forming atomizers and related structures and atomizers produced thereby, which are configured to avoid the problems associated with the above-noted start and stop winding process. The heating elements produced in accordance with the description provided below may be employed with a variety of smoking articles. However, the heating elements may, by way of example, may be employed in embodiments of the above-described smoking articles.

FIG. 13 illustrates an input 400 for production of a plurality of atomizers. As illustrated, the input 400 comprises a liquid transport element 402 and a wire 404. The liquid transport element 402 and the wire 404 may comprise any suitable material, such as one of the example embodiments of materials described above. Further, the particular cross-sectional shape of the liquid transport element 402 and the wire 404 may vary, and the cross-sectional areas thereof may be constant or vary along the length thereof. In this regard, the liquid transport element 402 and the wire 404 are generally described herein and illustrated as defining round cross-sectional shapes having constant cross-sectional areas along the longitudinal lengths thereof. However, various other embodiments of cross-sectional shapes may be employed, such as square, rectangular, or triangular.

As illustrated, the wire 404 continuously extends along a longitudinal length of the liquid transport element 402. As used herein, the term continuously extending refers to a relationship between the liquid transport element 402 and the wire 404 in which the wire is coextensive along the longitudinal length of the liquid transport element. By contrast, the term continuously extending excludes the above-described embodiments of heating elements produced by start and stop winding methods and which extend along only a portion of the longitudinal length of the atomizer.

Thus, the wire 404 according to the present disclosure defines a plurality of heating elements 406 along the longitudinal length of the input 400. The input 400 may be cut at spaced intervals to define a plurality of atomizers 408 respectively comprising a segment of the liquid transport element 402 and one of the heating elements 406 defined by the wire 404. In this regard, the input 400 may be cut along the lines 410 to separate the input 400 into the atomizers 408. Due to the wire 400 continuously extending along the longitudinal length of the liquid transport element 402 in the input 400, the wire will also continuously extend along the longitudinal length of the segment of the liquid transport element when divided into individual atomizers 408.

As further illustrated in FIG. 13, the wire 404 may define a plurality of coils 412. In some embodiments, as illustrated in FIG. 13, the wire 404 may be continuously wound about the liquid transport element 402. The term continuously wound, as used herein, refers to a wound configuration in which the angular position of the wire 404 about the liquid transport element 402 continuously changes along the longitudinal length of the liquid transport element. Thus, the wire 404 may repeatedly wrap about the perimeter of the liquid transport element 402, as illustrated in FIG. 13 with the coils 412 continuously extending along the longitudinal length thereof. Thus, a plurality of interconnected heating elements may be formed by a single wire. In other words, a single wire may extend along and define a plurality of heating elements, each respectively useable as an atomizer.

FIG. 14 illustrates an enlarged view of the input 400 at section A from FIG. 13, including a view of one of the heating elements 406. As illustrated, in addition to the heating element 406, the wire 404 may define a first end portion 414*a* and a second end portion 414*b* (collectively, "end portions 414"). Further, the heating element 406 may comprise a first contact portion 416*a* and a second end portion 416*a* (collectively, "contact portions 416") and a heating portion 418. The contact portions 416 may be positioned between the end portions 414 and the heating portion 418 may be positioned between the contact portions.

The coils 412 may define a pitch that varies along the longitudinal length of each atomizer 408. Pitch refers to a distance from a center of one coil 412 to a center of an adjacent coil. The coils 412 of the end portions 414 may define a first pitch 420, the coils of the contact portions 416 may define a second pitch 422, and the coils of the heating portion 418 may define a third pitch 424.

Thus, although not required, in some embodiments the pitch 420 of the first end portion 414*a* may be substantially equal to the pitch of the second end portion 414*b*. Similarly, although not required, the pitch 422 of the first contact portion 416A may be substantially equal to the pitch of the second contact portion 416B. Further, it should be noted that transitions between the end portions 414 and the contact portions 416 and between the contact portions and the heating portion 418 may result in the pitch of the coils 412 varying over the length of the individual portions. In this regard, the pitch of the coils of a particular portion of the wire 404, as used herein, refers to an average pitch of the coils over the length of the referenced portion.

In some embodiments the second pitch 422 may be less than the first pitch 420, and the third pitch 424 may be less than the first pitch and greater than the second pitch. As described below, this configuration of the pitches 420, 422, 424 of the end portions 414, the contact portions 416, and the heating portion 418 may provide particular benefits in terms of the functionality and cost of the atomizers 408. In one embodiment the second pitch 422 of the contact portions 416 may be substantially equal to a cross-sectional width of the wire 404. For example, in embodiments in which the wire 404 defines a round cross-section, the second pitch 422 may be substantially equal to a diameter of the wire. This pitch corresponds to a configuration in which the coils 412 of the wire 404 are substantially in contact with one another. As described below, this configuration may have certain advantages. However, various other embodiments of pitches of the coils may be employed in other embodiments.

In one embodiment a ratio of the third pitch 424 to the second pitch 422 may be from about two though eight to one, and in one embodiment about four to one. The ratio of the first pitch 420 to the second pitch 422 may be from about eight through thirty-two to one, and in one embodiment about sixteen to one. The ratio of the first pitch 420 to the third pitch 424 may be from about one through sixteen to one, and in one embodiment about four to one.

The input 400 may be employed to relatively inexpensively and rapidly produce atomizers 408. In this regard, by coupling the wire 404 to the liquid transport element 402 in a manner by which the wire continuously extends along the longitudinal length of the liquid transport element, the input 400 may be produced continuously to the extent of the length of the material defining the wire and the liquid transport element. Thereafter, or concurrently therewith, the input 400 may be divided into the plurality of atomizers 408. Thus, the atomizers 408 may be more efficiently produced as compared to the above-described stop and start winding process or other embodiments of processes that require discrete production of heating elements.

As noted above, the input 400 may be divided into a plurality of atomizers 408. As illustrated in FIG. 15, when the input 400 is divided into a plurality of atomizers 408, the wire 404 extends from a first liquid transport element end 426*a* to a second liquid transport element end 426*b* (collectively, "liquid transport element ends 426"). In this regard, the wire 404 continuously extends along the entirety of the longitudinal length of the liquid transport element 402.

More particularly, FIG. 15 illustrates attachment of the atomizer 408 to certain components of the above-described cartridge 200. In this regard, the atomizer 408 may be employed in use in a variety of aerosol delivery devices, such as cartridges for smoking articles. Thus, use of the atomizer 408 with components previously described and included in the cartridge 200 is illustrated by way of example, and it should be understood that the atomizers 408 produced from the input 400 may be employed in a variety of other aerosol delivery devices.

As illustrated in FIG. 15, during assembly of a cartridge, in some embodiments the heater terminals 220 may be coupled to the base 202 prior to coupling the atomizer 408 to the heater terminals. In this regard, the base 202 may be employed to hold the heater terminals 220 in place so as to facilitate attachment of the atomizer 408 to the heater terminals. However, in other embodiments the heater terminals 220 may be coupled to the atomizer 408 prior to coupling the heater terminals to the base 202. As further illustrated in FIG. 15, the contact portions 416 of the heating element 406 may respectively contact one of the heater terminals 220. More particularly, the contact portions 416 of the heating element 406 may respectively contact one of the tabs 234 of the heater terminals 220. The tabs 234 may be connected to the connector portions 416 of the heater element 406 by crimping, welding, or any other method or mechanism.

The contact portions 416 may define a plurality of coils 412. In the illustrated embodiment (see, e.g., FIG. 14), the contact portions 416 respectively comprise 4 coils. However, various other numbers of coils 412 may be employed in other embodiments. By way of example, in some embodiments the contact portions 416 may comprise about 3 coils to about 5 coils. Use of a plurality of coils 412 may assist in forming a connection with the tabs 234 of the heater terminals 220. Further, providing the contact portions 416 with a relatively small pitch 422, for example in which the coils 412 thereof touch one another, may further facilitate establishing an electrical connection between the contact portions and the heater terminals 220. In this regard, the wire 404 may define a relatively greater surface area at the contact portions 416, which may facilitate connection to the tabs 234.

Further, the liquid transport element 402 may be bent about the heater terminals 220 such that the liquid transport element ends 426 are positioned proximate the base 202. As the liquid transport element 402 is bent about the heater terminals 220, the end portions 414 of the wire 404 may also bend and come into contact with the heater terminals. Since the wire 404 extends from the first liquid transport element end 426*a* to the second liquid transport element end 426*b*, the wire may assist in maintaining the liquid transport element 402 in the bent configuration. In this regard, as the liquid transport element 402 is bent, the wire 404 may plastically deform and retain the bent configuration. Thus, coupling between the liquid transport element 402 and the heater terminals 220 may be improved.

FIG. 16 illustrates a modified cross-sectional view through a cartridge 500 comprising the components of the cartridge 200 illustrated in FIG. 2, with the atomizer 208 replaced with the atomizer 408 produced from the input 400. Thus, as illustrated, the cartridge 500 includes the base 202 defining the connector end 246 configured to engage a control body. Further, the cartridge 500 includes the reservoir substrate 210 configured to hold an aerosol precursor composition. The reservoir substrate 210 defines the cavity 252 extending between the first reservoir end 254*a* and the second reservoir end 254*b*, wherein the first reservoir end is positioned proximate the base 202.

The atomizer 408 may extend through the cavity 252 of the reservoir substrate 210. The reservoir substrate 210 may define the grooves 256 at the cavity 252 extending from the first reservoir end 254*a* to the second reservoir end 254*b*. In this regard, the atomizer 408 may define the above-described bent configuration in which the liquid transport element 402 and the wire 404 are bent about the heater terminals 220. As illustrated, the liquid transport element 402 may define a first distal arm 428*a* and a second distal arm 428*b* (collectively, "distal arms 428") and a center section 428*c*.

The distal arms 428 of the liquid transport element 402 may be received in the grooves 256 at the cavity 252. As further illustrated in FIG. 16, the end portions 414 of the wire 404 may also be respectively received in the grooves 256. In this regard, the end portions 414 of the wire 404 may be at least partially positioned between the liquid transport element 402 and the reservoir substrate 210. However, as a result of employing a relatively coarse wind at the end portions 414, in which the pitch 420 is relatively large, the reduction in fluid transfer from the reservoir substrate 210 to the liquid transport element 402 may be relatively small. In this regard, in the illustrated embodiment, each of the end portions 414 defines six coils 412, which are spread across a relatively greater longitudinal length of the liquid transport element 404 than the contact portions 416. However, in other embodiments the end portions may define a smaller number or a larger number of the coils. By way of example, the end portions may comprise from about three coils to about seven coils in some embodiments. It is further of note that employing a relatively large pitch 420 of the coils 412 at the end portion 414 may reduce the material costs associated with the atomizer 408 by reducing the amount of the wire 404 employed to produce the atomizers.

Further, as a result of the end portions 414 of the wire 404 being in contact with the heater terminals 220, an electrical connection is formed therebetween. However, the end portions 414 of the wire 404 will be at substantially the same electrical potential as the heater terminals 220, and hence the end portions of the wire will substantially avoid producing any heat. In this regard, the first end portion 414*a* will be at substantially the same electrical potential as the first contact portion 416*a*, and the second end portion 414*b* will be at substantially the same electrical potential as the second contact portion 416*b* because the contact portions 416 are also in contact with the heater terminals 220. Accordingly, despite the wire 404 extending to the liquid transport element ends 426, heat may only be produced at the heating portion 418. Accordingly, the heating element 406 may directly heat only the center section 428*c* of the liquid transport element 402, which may be desirable to control the production of aerosol by controlling the amount of aerosol precursor exposed to the heat produced by the heating element 406.

Further, the amount of heat directed to the center section 428*c* of the liquid transport element 402 may be controlled by the pitch 424 of the coils 412 at the heating portion 418 of the wire. In this regard, the pitch 424 of the coils 412 may be relatively less than the pitch 420 of the coils at the end sections 414 but less than the pitch 422 of the coils at the contact portions 416. By ensuring that the coils 412 are not spaced too far apart, the liquid transport element 402 may be heated to a sufficient degree to produce aerosol vapors. Further, by providing gaps between the coils 412 at the heating portion 418, the vaporized aerosol may be able to escape from the liquid transport element 402. In the illustrated embodiment the heating portion 418 comprises six coils 412. However, a larger or smaller number of coils may be provided in other embodiments. For example, the heating portion may comprise from about 4 coils to about 9 coils in other embodiments.

Note that the above-described atomizer comprising a heating element with a variable spacing of coils thereof may be employed in a variety of embodiments of cartridges for aerosol delivery devices. In this regard, FIG. 17 illustrates a partially exploded view of an aerosol delivery device 600 including a control body 700, which is illustrated in an assembled configuration, and a cartridge 800, which is illustrated in an exploded configuration. The control body 700 may include various components as described above. For example, the control body 700 may include an outer tube 702 and a receptacle or coupler 704 and an end cap 706 coupled to opposing ends of the outer tube. Various internal components inside the outer tube 702 may include, by way of example, a flow sensor, a control component, and an electrical power source (e.g., a battery), and a light emitting diode (LED) element. However, the control body 700 may include additional or alternative components in other embodiments.

As illustrated, the cartridge 800 may comprise a base shipping plug 802, a base 804, a control component terminal 806, an electronic control component 808, a flow tube 810, an atomizer 812, a reservoir substrate 814, an external shell 816, a label 818, a mouthpiece 820, and a mouthpiece shipping plug 822 according to an example embodiment of the present disclosure. Many of these components are substantially similar to the components of the cartridges described above. Accordingly, only differences with respect to the previously-described embodiments of cartridges will be described below.

In this regard, in one embodiment the electronic control component 808 may comprise a single-piece printed circuit board assembly. The electronic control component 808 may include a ceramic substrate, which may comprise about 96% alumina ceramic in one embodiment. This material is inorganic, non-reactive, non-degrading, and non-porous. Use of such a ceramic material may be preferable in that it may define a robust, dimensionally-stable part without requiring a separate supporting structure. Further, such a ceramic material may allow for adhesion of a coating thereto. For example, a component side of the electronic control component 808 may comprise a coating material such as a chloro-substituted poly (para-xylylene) commercially available as Parylene C from Specialty Coating Systems, Inc., or any other coating or other sealant/barrier coating configured to protect components of the circuit board from liquid and moisture. The sealant/barrier coating may also provide the electronic control component 808 with a decreased coefficient of friction, which may facilitate an axial assembly process of the cartridge 800.

Further, the mouthpiece shipping plug 822 is configured to engage openings in the mouthpiece 820 prior to use of the cartridge 800 in order to prevent entry of contaminants through the openings in the mouthpiece. Similarly, the base shipping plug 802 is configured to couple to an inner periphery of the base 804 to protect the base from damage or contamination during transport and storage. Further, the label 818 may serve as an exterior member providing the cartridge 800 with identifying information.

FIG. 18 illustrates a perspective view of the cartridge 800 in a partially assembled configuration. More particularly, FIG. 18 illustrates components of the cartridge 800 in a partially assembled configuration corresponding to the configuration illustrated in FIG. 8. Thus, briefly, FIG. 18 illustrates a configuration in which the control component terminal 806 has been coupled to the base 804, the electronic control component 808 has been coupled to the electronic control component terminal, a first heater terminal 834*a* and a second heater terminal 834*b* (collectively, "heater terminals 834") has been coupled to the base, the flow tube 810 is received between the heater terminals, a heating element 840 is wound about a liquid transport element 838 and extends along the length thereof, the heating element is coupled to first and second tabs 836*a*, 836*b* of the heater terminals to complete the atomizer 812, and the reservoir substrate 814 is received around the atomizer.

The reservoir substrate 814 may define a cavity 852 extending therethrough from a first reservoir end 854*a* to a second reservoir end 854*b* (collectively, "reservoir ends 854"), wherein the first reservoir end is positioned proximate the base 804. In this regard, the reservoir substrate 814 may define a hollow tubular configuration. The reservoir substrate 814 can comprise one or more of various materials and can be formed in a variety of different manners. In one embodiment the reservoir substrate 814 can be formed from a plurality of combined layers that can be concentric or overlapping. For example, the reservoir substrate 814 can be a continuous sheet of a material that is rolled such that the ends thereof meet along a joint 856 to form the hollow tubular configuration, or multiple layers of the material may be wrapped thereabout. Thus, the reservoir substrate 814 may conform to the shape of the components received in the cavity 852 such as the atomizer 812.

As illustrated in FIGS. 17 and 18, in some embodiments the cartridge 800 may additionally include the flow tube 810. As illustrated in FIG. 18, the flow tube 810 may be positioned between, and held in place by, the terminals 834. More particularly, the flow tube 810 may define first 858*a* and second 858*b* opposing grooves (collectively, "grooves 858"). The grooves 858 may be sized and shaped to respectively receive one of the terminals 834 therein. In this regard, in some embodiments the flow tube 810 may define a generally round outer perimeter, with the exception of the grooves 858. Thus, the flow tube 810 may be received inside the cavity 852 defined through the reservoir substrate 814. Accordingly, the flow tube 810 may additionally or alternatively be held in place by the reservoir substrate 814. The flow tube 810 may also be held in place via contact with the electronic control component 808 in some embodiments.

The flow tube 810 may be configured to direct a flow of air received from the base 804 to the heating element 840 of the atomizer 812. More particularly, as illustrated in FIG. 18, the flow tube 810 may define a through hole 860 extending along the length of the center of the flow tube configured to receive air from the base 804 and direct it to the heating element 840. Accordingly, the size of the through hole 860 may be selected to define a desired velocity of air directed to the heating element 840. Accordingly, a desired amount of aerosol may be delivered to the air as the air passes the heating element 840. For example, the through hole 860 may taper from a relatively larger diameter to a relatively smaller diameter proximate the heating element 840. However, in other embodiments the through hole 860 may define a substantially constant or increasing diameter.

In some embodiments the flow tube 810 may comprise a ceramic material. For example, the flow tube 810 may comprise 96.5% aluminum tri oxide in one embodiment. This material may provide heat resistance which may be desirable due to proximity to the heating element 840. However, the flow tube 810 may be formed from various other materials in other embodiments.

The reservoir substrate 814 includes an exterior surface 862 that can be substantially shaped and adapted to conform to an interior surface of the external shell 816 (see, FIG. 17). Accordingly, the external shell 816 may be received over the reservoir substrate 814 and coupled to the base 804. In a fully assembled configuration the cartridge may appear substantially similar to the cartridge 200 illustrated in FIG. 10 with the base shipping plug, the mouthpiece shipping plug, and the label coupled thereto.

Although a wire is generally described above as being continuously wound about a liquid transport element, the wire may be configured in various other manners in which the wire continuously extends along the longitudinal length of the liquid transport element in other embodiments. In this regard, FIG. 19 illustrates an enlarged view of a portion of an input 900 comprising a liquid transport element 902 and a wire 904 extending along the longitudinal length of the liquid transport element. As illustrated, the wire 904 may be wound about the liquid transport element 902 to define a heating element 906. The wire 904 may define a plurality of coils 912 wound about the liquid transport element 902 at the heating element 906.

In addition to the heating element 906, the wire 904 may define a first end portion 914*a* and a second end portion 914*b* (collectively, "end portions 914"). Further, the heating element 906 may comprise a first contact portion 916*a* and a second end portion 916*a* (collectively, "contact portions 916") and a heating portion 918. The contact portions 916 may be positioned between the end portions 914 and the heating portion 918 may be positioned between the contact portions.

Thus, the liquid transport element 902 and the contact portions 916 and the heating portion 918 of the input 900 may be substantially similar to the corresponding components of the input 400 described above, and hence additional details with respect to these components will not be repeated for purposes of brevity. However, whereas the embodiment of the input 400 illustrated in FIG. 14 includes a plurality of coils 412 at the end portions 414, the end portions 914 of the input 900 illustrated in FIG. 19 may not include coils. Rather, as illustrated in FIG. 19, in some embodiments the end portions 914 may extend substantially parallel to the longitudinal length of the liquid transport element 902. In this regard, the end portions of the atomizers described herein may define a plurality of configurations. Embodiments in which the end portions are wound about the liquid transport element may be desirable in that coils positioned at the end sections may assist in retaining a coupling between the wire and the liquid transport element and retaining the atomizer in a bent configuration, as described above. However, embodiments in which the end portions of the wire extend substantially parallel to the longitudinal length of the liquid transport element may be desirable in that less wire may be needed to produce the atomizers, and hence material costs may be further reduced.

A method of forming a plurality of atomizers is also provided. As illustrated in FIG. 20, the method may comprise providing a liquid transport element at operation 1002. Further, the method may include providing a wire at operation 1004. The method may additionally include coupling the wire to the liquid transport element such that the wire extends continuously along a longitudinal length of the liquid transport element and defines a plurality of heating elements at operation 1006, the heating elements respectively comprising a plurality of coils of the wire.

In some embodiments coupling the wire to the liquid transport element at operation 1006 may comprise continuously winding the wire about the liquid transport element. Further, winding the wire about the liquid transport element may comprise winding the wire to define a plurality of end portions defining a first pitch and winding the wire such that each of the heating elements comprises a plurality of contact portions positioned between the end portions and defining a second pitch and a heating portion positioned between the contact portions and defining a third pitch. The second pitch may be less than the first pitch, and the third pitch may be less than the first pitch and greater than the second pitch. In some embodiments the second pitch may be substantially equal to a diameter of the wire.

In some embodiments, during winding of the wire about the liquid transport element, the tension on one or both of the liquid transport element and the wire may be controlled. In this regard, winding the wire too loosely about the liquid transport element may result in the heating portion being out of contact with the liquid transport element, which could result in high temperatures of the heating element and poor vaporization during operation of the resultant atomizer. Further, winding the wire too tightly about the liquid transport element may result in impediment of the fluid flow through the liquid transport element. Accordingly, the tensions on the wire and the liquid transport element may be maintained at such levels wherein the wire remains in contact with the liquid transport element but does not substantially compress the liquid transport element.

In some embodiments the method may further comprise cutting the liquid transport element and the wire at one of the end portions to separate one of the heating elements and a segment of the liquid transport element therefrom at operation 1008. Further, the method may include providing a first heater terminal and a second heater terminal at operation 1010 and respectively engaging the contact portions of the one of the heating elements with the first heater terminal and the second heater terminal at operation 1012. Additionally, the method may include bending the one of the heating elements and the segment of the liquid transport element about the first heater terminal and the second heater terminal at operation 1014. The method may also include engaging the end portions with one of the first heater terminal and the second heater terminal at operation 1016.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An input for production of a plurality of atomizers, the input comprising:

a liquid transport element; and a wire extending along at least a portion of a longitudinal length of the liquid transport element and defining a plurality of heating elements, the heating elements respectively comprising a plurality of coils of the wire, the wire defining at each of the heating elements a plurality of contact portions and a heating portion positioned between the contact portions, a pitch of the wire being greater at the heating portion than the pitch of the wire at the contact portions.

2. The input of claim 1, wherein the wire is continuously wound about the liquid transport element.

3. The input of claim 2, wherein the wire further defines a plurality of end portions, wherein the pitch of the wire at the end portions is greater than the pitch of the wire at the heating portion.

4. The input of claim 3, wherein the pitch of the wire at the contact portions is substantially equal to a diameter of the wire.

5. An atomizer for an aerosol delivery device, the atomizer comprising:

a liquid transport element extending between a first liquid transport element end and a second liquid transport element end; and a wire extending along at least a portion of the liquid transport element between the first liquid transport element end and the second liquid transport element end and defining a heating element comprising a plurality of coils of the wire, the wire defining at the heating element a plurality of contact portions and a heating portion positioned between the contact portions, a pitch of the wire being greater at the heating portion than the pitch of the wire at the contact portions.

6. The atomizer of claim 5, wherein the wire is continuously wound about the liquid transport element.

7. The atomizer of claim 6, wherein the wire further defines a plurality of end portions, wherein the pitch of the wire at the end portions is greater than the pitch of the wire at the heating portion.

8. The atomizer of claim 7, wherein the pitch of the wire at the contact portions is substantially equal to a diameter of the wire.

9. The atomizer of claim 7, further comprising a first heater terminal and a second heater terminal, wherein the contact portions of the heating element respectively contact one of the first heater terminal and the second heater terminal.

10. The atomizer of claim 9, wherein the end portions respectively contact one of the first heater terminal and the second heater terminal.

11. A cartridge for an aerosol delivery device, the cartridge comprising:

a base defining a connector end configured to engage a control body;

a reservoir configured to hold an aerosol precursor composition, the reservoir defining a cavity extending from a first reservoir end to a second reservoir end, wherein the first reservoir end is positioned proximate the base; and an atomizer comprising:

a liquid transport element extending between a first liquid transport element end and a second liquid transport element end; and a wire extending along at least a portion of the liquid transport element between the first liquid transport element end and the second liquid transport element end and defining a heating element comprising a plurality of coils of the wire, the wire defining at the heating element a plurality of contact portions and a heating portion positioned between the contact portions, a pitch of the wire being greater at the heating portion than the pitch of the wire at the contact portions.

12. The cartridge of claim 11, wherein the wire is continuously wound about the liquid transport element.

13. The cartridge of claim 12, wherein the wire further defines a plurality of end portions, wherein the pitch of the wire at the end portions is greater than the pitch of the wire at the heating portion.

14. The cartridge of claim 13, wherein the pitch of the wire at the contact portions is substantially equal to a diameter of the wire.

15. The cartridge of claim 13, wherein the atomizer further comprises a first heater terminal and a second heater terminal, and wherein the contact portions of the heating element respectively contact one of the first heater terminal and the second heater terminal.

16. The cartridge of claim 15, wherein the end portions respectively contact one of the first heater terminal and the second heater terminal.

17. A method of forming atomizers, the method comprising:

providing a liquid transport element;

providing a wire; and winding the wire about the liquid transport element such that the wire extends along at least a portion of a longitudinal length of the liquid transport element and defines a plurality of heating elements, the heating elements respectively comprising a plurality of coils of the wire, the wire defining at each of the heating elements a plurality of contact portions and a heating portion positioned between the contact portions, a pitch of the wire being greater at the heating portion than the pitch of the wire at the contact portions.

18. The method of claim 17, wherein winding the wire about the liquid transport element comprises continuously winding the wire about the liquid transport element.

19. The method of claim 18, wherein winding the wire about the liquid transport element comprises winding the wire to define a plurality of end portions, wherein the pitch of the wire at the end portions is greater than the pitch of the wire at the heating portion.

20. The method of claim 19, wherein the pitch of the wire at the contact portions is substantially equal to a diameter of the wire.

21. The method of claim 19, further comprising cutting the liquid transport element and the wire at one of the end portions to separate one of the heating elements and a segment of the liquid transport element therefrom.

22. The method of claim 21, further comprising providing a first heater terminal and a second heater terminal; and respectively engaging the contact portions of the one of the heating elements with the first heater terminal and the second heater terminal.

23. The method of claim 22, further comprising bending the one of the heating elements and the segment of the liquid transport element about the first heater terminal and the second heater terminal.

24. The method of claim 23, further comprising respectively engaging the end portions with one of the first heater terminal and the second heater terminal.

* * * * *